(12) United States Patent
Vaz et al.

(10) Patent No.: US 11,341,636 B2
(45) Date of Patent: *May 24, 2022

(54) METHODS AND SYSTEMS FOR AN ADAPTIVE FIVE-ZONE PERFUSION SCAN

(71) Applicant: GE Precision Healthcare LLC, Milwaukee, WI (US)

(72) Inventors: Michael Sarju Vaz, Milwaukee, WI (US); Nitya Talasila, Aurora, IL (US); Bradley Gabrielse, Brookfield, WI (US); Ryan Forbes, Waukesha, WI (US); David Joseph Pitterle, Waukesha, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 130 days.

This patent is subject to a terminal disclaimer.

(21) Appl. No.: 16/672,314

(22) Filed: Nov. 1, 2019

(65) Prior Publication Data

US 2021/0133960 A1    May 6, 2021

(51) Int. Cl.
*G06T 7/00* (2017.01)
*G06T 7/11* (2017.01)
(Continued)

(52) U.S. Cl.
CPC .............. *G06T 7/0012* (2013.01); *A61B 6/03* (2013.01); *A61B 6/481* (2013.01); *A61B 6/488* (2013.01); *G06N 20/00* (2019.01); *G06T 7/11* (2017.01); *G06T 2207/10072* (2013.01); *G06T 2207/20036* (2013.01); *G06T 2207/20084* (2013.01);
(Continued)

(58) Field of Classification Search
CPC .......... A61B 6/03; A61B 6/032; A61B 6/481; A61B 6/488; A61B 6/507; G06T 7/0012; G06T 2207/10072; G06T 2207/20036; G06T 2207/20084; G06T 2207/20112;
(Continued)

(56) References Cited

U.S. PATENT DOCUMENTS

| 5,400,378 A | 3/1995 | Toth |
| 6,023,494 A | 2/2000 | Senzig et al. |

(Continued)

FOREIGN PATENT DOCUMENTS

CN       101277648 A       10/2008

OTHER PUBLICATIONS

Vaz, M. et al., "Methods and Systems for Timing a Second Contrast Bolus," U.S. Appl. No. 16/672,261, filed Nov. 1, 2019, 84 pages.
(Continued)

*Primary Examiner* — Katrina R Fujita
(74) *Attorney, Agent, or Firm* — McCoy Russell LLP

(57) ABSTRACT

Methods and systems are provided for adaptive scan control. In one embodiment, a method includes, upon a first injection of a contrast agent, processing acquired projection data of a monitoring area of a subject to measure a contrast signal of the contrast agent, determining when each of a plurality of zones of a contrast scan are estimated to occur based on the contrast signal, generating a scan prescription for the contrast scan based on when each of the plurality of zones are estimated to occur, and upon a second injection of contrast agent, performing the contrast scan according to the scan prescription.

20 Claims, 14 Drawing Sheets

(51) Int. Cl.
*A61B 6/00* (2006.01)
*A61B 6/03* (2006.01)
*G06N 20/00* (2019.01)

(52) U.S. Cl.
CPC ............... *G06T 2207/20112* (2013.01); *G06T 2207/30101* (2013.01)

(58) Field of Classification Search
CPC ........ G06T 2207/30101; G06N 3/0454; G06N 20/00
See application file for complete search history.

(56) References Cited

U.S. PATENT DOCUMENTS

| | | | |
|---|---|---|---|
| 6,236,706 B1 | 5/2001 | Hsieh | |
| 6,256,368 B1 | 7/2001 | Hsieh et al. | |
| 6,891,918 B2 | 5/2005 | Drummond et al. | |
| 7,145,982 B2 | 12/2006 | Ikeda et al. | |
| 7,983,460 B2 | 7/2011 | Licato et al. | |
| 8,428,694 B2* | 4/2013 | Kalafut | A61B 6/481 600/431 |
| 9,327,143 B2 | 5/2016 | Gillece et al. | |
| 9,486,176 B2 | 11/2016 | Goyal | |
| 9,517,042 B2 | 12/2016 | Hsieh et al. | |
| 9,622,717 B2 | 4/2017 | Londt et al. | |
| 10,349,909 B2 | 7/2019 | Okerlund et al. | |
| 2007/0213662 A1* | 9/2007 | Kalafut | A61M 5/007 604/96.01 |
| 2009/0247864 A1* | 10/2009 | Rauscher-Scheibe | A61B 6/032 600/431 |
| 2009/0316970 A1* | 12/2009 | Kemper | G06T 7/0012 382/131 |
| 2010/0066756 A1* | 3/2010 | Yang | G06T 7/0012 345/593 |
| 2011/0257519 A1* | 10/2011 | Bjornerud et al. | A61B 5/055 600/431 |
| 2013/0211247 A1* | 8/2013 | Kalafut | G16H 50/50 600/432 |
| 2017/0086772 A1 | 3/2017 | Vaz et al. | |
| 2017/0178338 A1* | 6/2017 | Yang | G06T 7/0016 |
| 2017/0209113 A1 | 7/2017 | Jackson et al. | |
| 2018/0049714 A1 | 2/2018 | Nett | |
| 2019/0038150 A1* | 2/2019 | Jang | G01R 33/5601 |
| 2019/0231288 A1 | 8/2019 | Profio et al. | |
| 2019/0313990 A1* | 10/2019 | Sahbaee Bagherzadeh | A61B 5/055 |

OTHER PUBLICATIONS

Vaz, M. et al., "Methods and Systems for an Adaptive Multi-Phase Angiography Scan," U.S. Appl. No. 16/672,281, filed Nov. 1, 2019, 85 pages.

Vaz, M. et al., "Methods and Systems for a Single-Bolus Angiography and Perfusion Scan," U.S. Appl. No. 16/672,336, filed Nov. 1, 2019, 85 pages.

Vaz, M. et al., "Methods and Systems for an Adaptive Four-Zone Perfusion Scan," U.S. Appl. No. 16/672,350, filed Nov. 1, 2019, 85 pages.

"The ONE Guides—4D Neurological Imaging," Cannon Medical Systems USA Website, Available Online at https://us.medical.canon/download/aq-one-club-guide-4d-neuro-imaging, Available Online at Early as Jan. 2010, 16 pages.

Hinzpeter, R. et al., "CT Angiography of the Aorta: Contrast Timing by Using a Fixed versus a Patient-specific Trigger Delay," University of Zurich Open Repository and Archive Website, Available Online at https://www.zora.uzh.ch/id/eprint/170529/1/radiol.2019182223.pdf, Available as Early as May 2019, 10 pages.

Lewis, C. et al., "Methods and Sytems for Protocol Management," U.S. Appl. No. 16/553,028, filed Aug. 27, 2019, 59 pages.

* cited by examiner

METHODS AND SYSTEMS FOR AN ADAPTIVE FIVE-ZONE PERFUSION SCAN

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care require two contrast boli for separate CT angiography (CTA) and CT perfusion (CTP) studies. Further, prior to performing CTA and CTP studies, typical methods first perform a timing bolus scan, wherein a small contrast bolus is administered to a patient and subsequent contrast levels within the patient are monitored to generate a CTP/CTA scan prescription personalized to the patient. However, the timing bolus scan alone takes five minutes, and performing CTA and CTP studies separately requires five to seven minutes between acquisitions to allow contrast washout.

BRIEF DESCRIPTION

In one embodiment, a method includes, upon a first injection of a contrast agent, processing acquired projection data of a monitoring area of a subject to measure a contrast signal of the contrast agent, determining when each of a plurality of zones of a contrast scan are estimated to occur based on the contrast signal, generating a scan prescription for the contrast scan based on when each of the plurality of zones are estimated to occur, and upon a second injection of contrast agent, performing the contrast scan according to the scan prescription.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
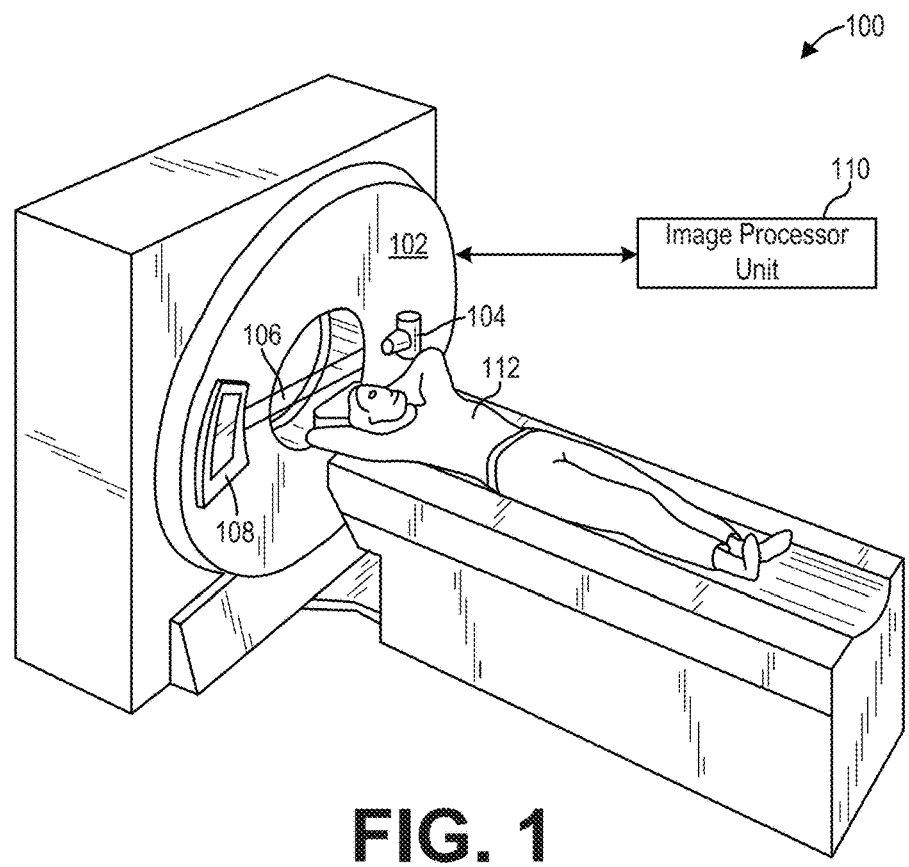
FIG. 1 shows a pictorial view of an imaging system, according to an embodiment.

Some diagnostic imaging protocols, such as protocols to diagnose acute stroke in a patient, include one or more contrast scans, where a contrast agent is administered to the patient prior to the diagnostic imaging scan. These diagnostic imaging protocols may include two contrast scans, such as a computed tomography (CT) angiography (CTA) scan followed by a CT perfusion (CTP) scan. In a CTA followed by a CTP (or in a CTP followed by a CTA), the decision of when to administer the second contrast agent bolus may be challenging, and if timed incorrectly, may result in non-diagnostic images and/or undesired patient outcomes. For example, if the second contrast agent bolus is administered too soon after the first contrast scan, diagnostic image quality of images acquired during the second contrast scan may be degraded due to venous contrast contamination from the first contrast agent bolus. However, if the second contrast agent bolus is administered too late after the first contrast scan, patient outcome (e.g., life expectancy, quality of life) may be impacted.

Thus, according to embodiments disclosed herein, the timing of a second contrast bolus administered after a first contrast bolus may be determined automatically based on an estimated arterial inflow function (AIF) curve and estimated venous outflow function (VOF) curve. The estimated AIF and VOF curves may be estimated based on an AIF signal measured upon the prior first contrast agent injection (e.g., during a prior timing bolus or during a prior contrast scan). The AIF signal may comprise a measured contrast level in a region of interest (e.g., an artery, such as the internal carotid artery) over a duration. The duration is relatively limited due to scan timing constraints (e.g., due to the need to begin the first contrast scan as quickly as possible after the timing bolus or first contrast bolus), and thus the entirety of the AIF curve and VOF curves may not be directly measured. Rather, the AIF signal may be entered as input to a machine learning (ML) model that may output the estimated AIF curve and estimated VOF curve (and/or time points of interest from the AIF and VOF curves, such as arterial peak, venous peak, and venous return to baseline). Based on the output of the ML model, the desired time for administration of the second contrast bolus relative to the administration of the first contrast bolus may be determined, and then the second contrast bolus may be administered at the desired time. For example, the desired time may be the return to baseline of the VOF curve (the venous return to baseline, VRTB) for the first contrast bolus. The amount of time from an injection of contrast agent to the VRTB for the patient may be determined from the estimated AIF and VOF curves, and once this amount of time has elapsed since the administration of the first contrast bolus, the second contrast bolus may be administered. In this way, the precise amount of time for when to administer the second contrast bolus may be determined for each patient using information already available during a standard contrast scan protocol, thereby reducing the likelihood that the images reconstructed from scan data acquired during the second contrast scan will be non-diagnostic due to venous contrast agent contamination while preventing undue delays in commencing the second contrast scan that could otherwise negatively impact patient outcomes.

Figure 2:
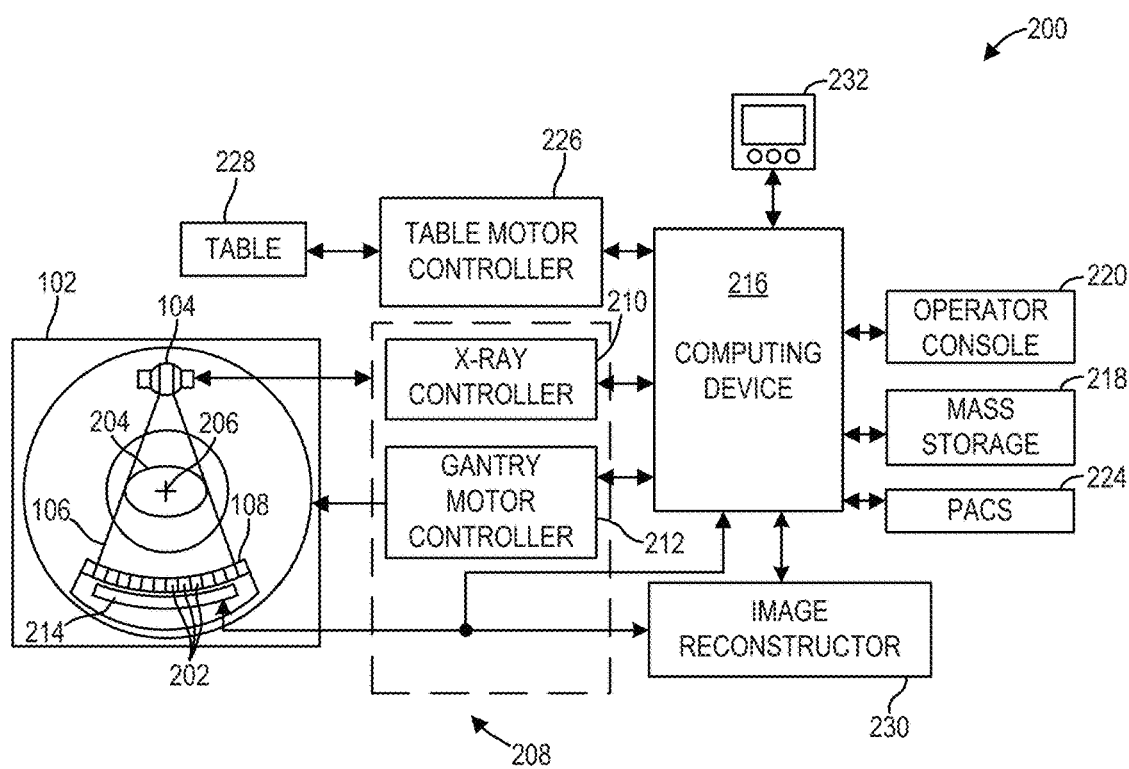
FIG. 2 shows a block schematic diagram of an exemplary imaging system, according to an embodiment.
Figure 3:
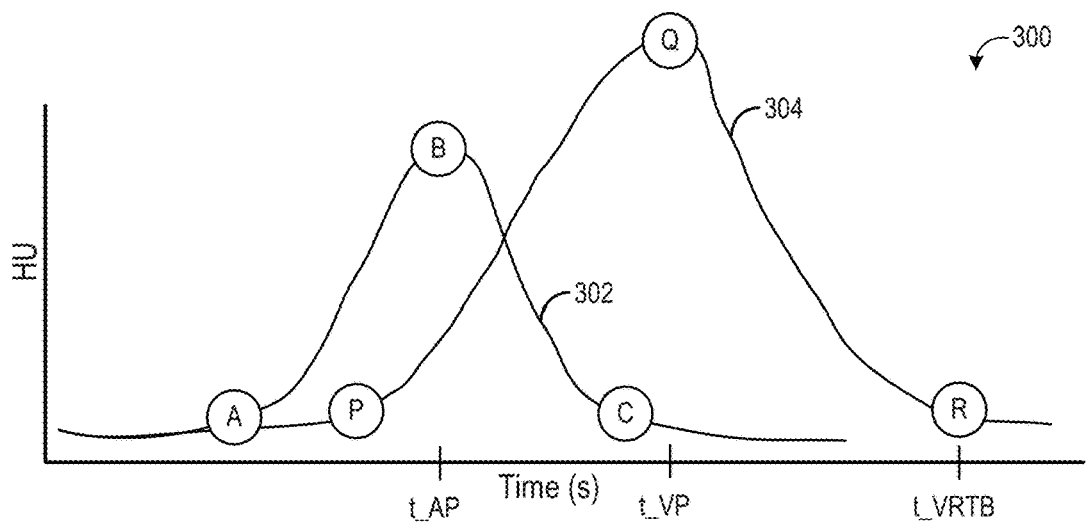
FIG. 3 shows a graph illustrating an example arterial inflow function (AIF) curve and an example a venous outflow function (VOF) curve generated during a contrast scan.
Figure 4:
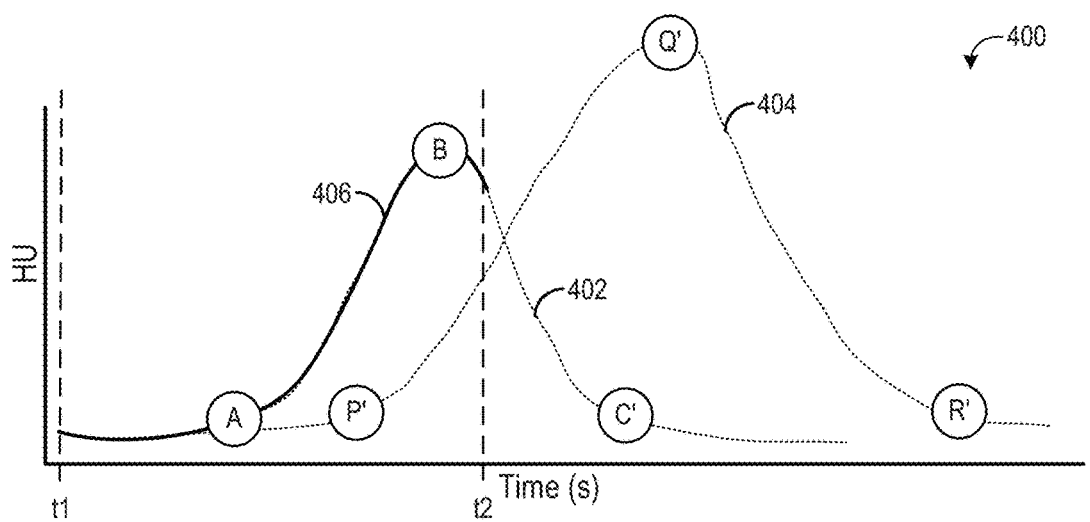
FIG. 4 shows a graph illustrating an estimated AIF curve and an estimated VOF curve generated according to an embodiment of the disclosure.
Figure 5:
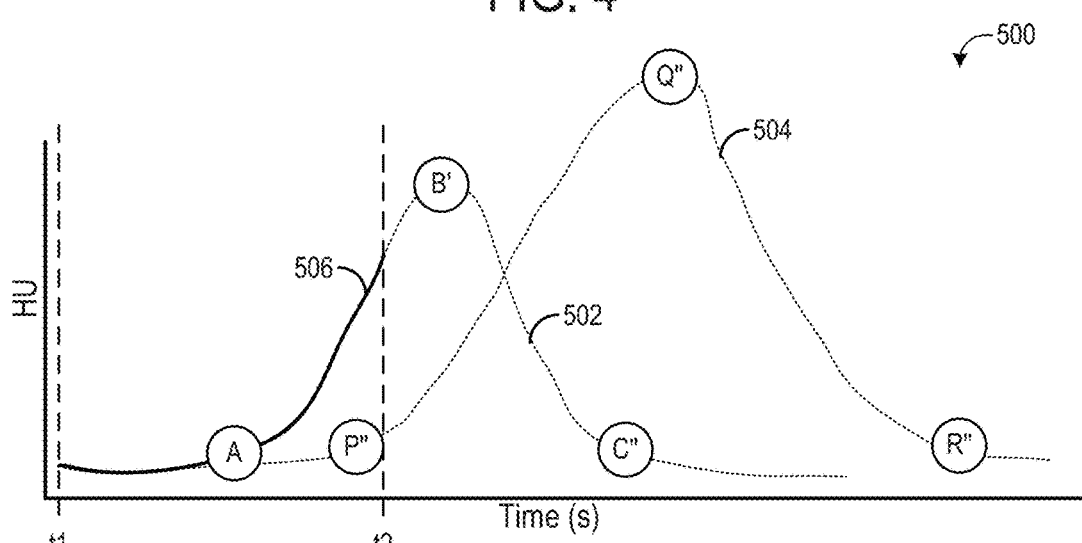
FIG. 5 shows a graph illustrating an estimated AIF curve and an estimated VOF curve generated according to another embodiment of the disclosure.
Figure 6:
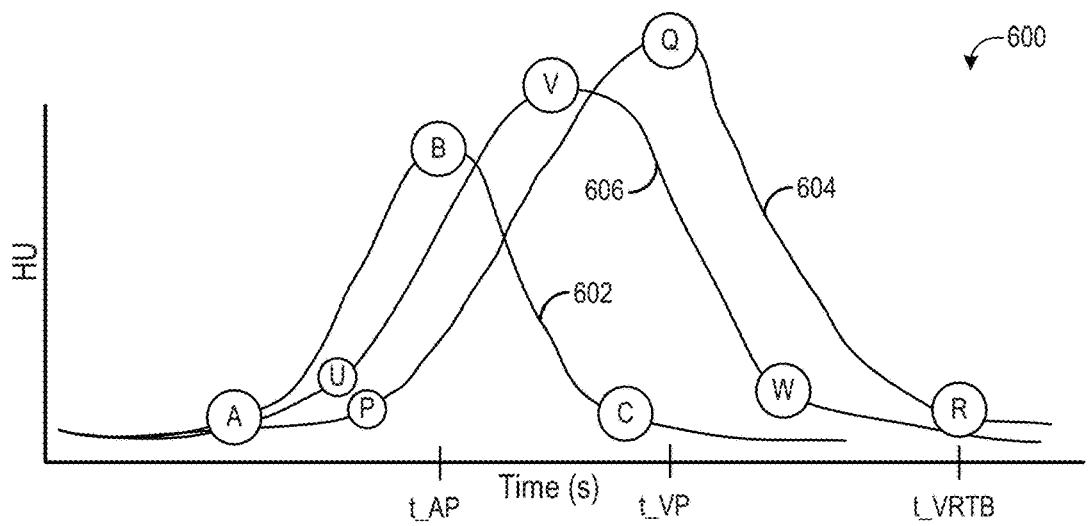
FIG. 6 shows a graph illustrating an example AIF curve, an example VOF curve, and an example tissue uptake curve (TUC) generated during a contrast scan.
Figure 7:
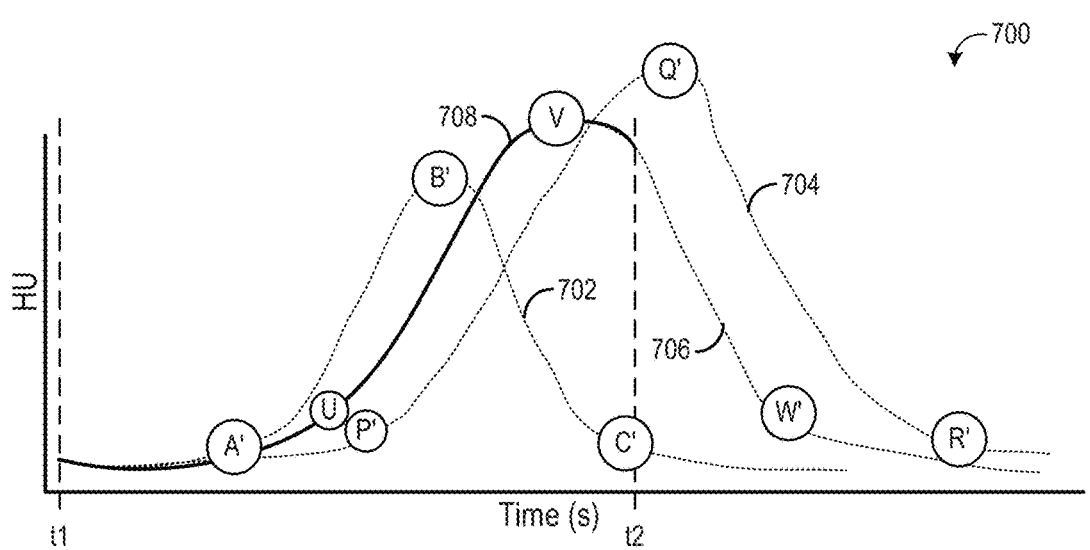
FIG. 7 shows a graph illustrating an estimated AIF curve, an estimated VOF curve, and an estimated TUC generated according to an embodiment of the disclosure.
Figure 8:
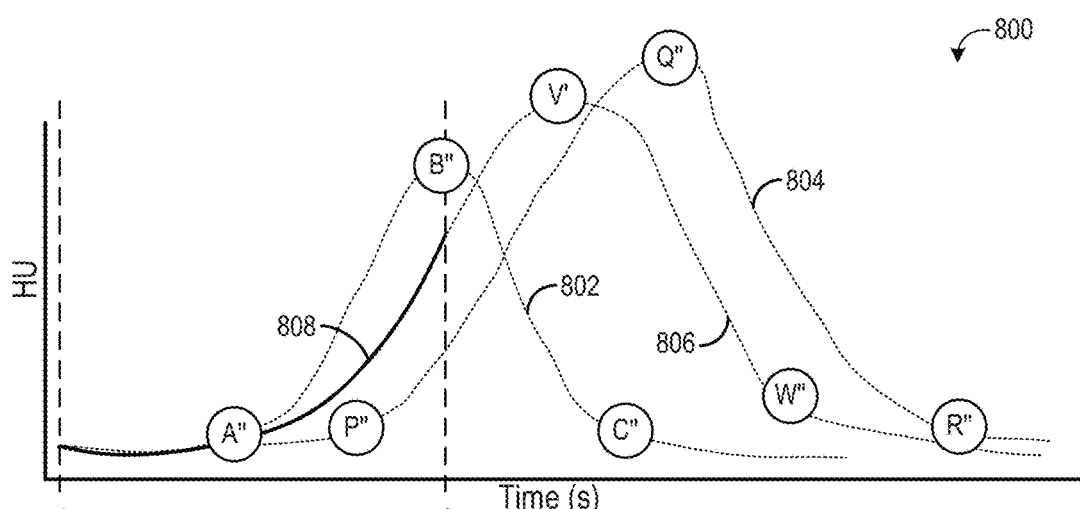
FIG. 8 shows a graph illustrating an estimated AIF curve, an estimated VOF curve, and an estimated TUC generated according to another embodiment of the disclosure.

An example of a computed tomography (CT) imaging system that may be used to perform the contrast scans in accordance with the present techniques is provided in FIGS. 1 and 2. As described above, the timing of the contrast scans may be dependent on the AIF and VOF curves of the contrast agent, which vary from patient to patient. FIG. 3 shows example AIF and VOF curves for a patient. A portion of the AIF curve may be directly measured prior to a first contrast scan commencing or during the first portion of the first contrast scan, and this portion may be used as input to a model to estimate the remaining AIF curve and the VOF curve for the patient, as shown in FIGS. 4 and 5. As another example, rather than measuring the AIF, tissue uptake of the contrast agent may be measured for a duration, and this measured portion of the tissue uptake curve (TUC) may be entered into a model to estimate the AIF and VOF curves. FIG. 6 shows example AIF, TUC, and VOF curves, while FIGS. 7 and 8 show example portions of the TUC that may be measured and used as input to estimate the AIF and VOF curves.

Figure 9:
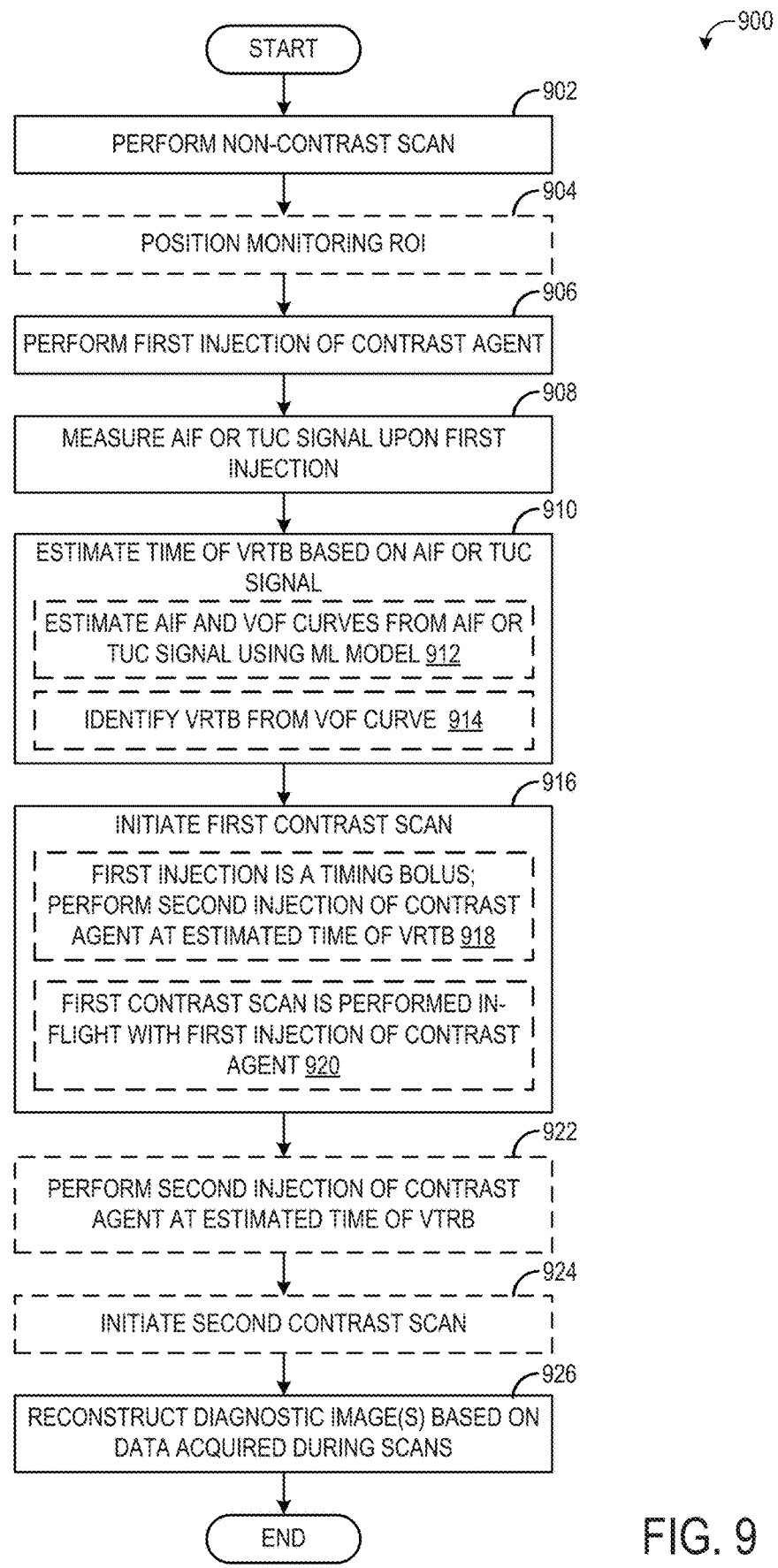
FIG. 9 is a flow chart illustrating a method for performing a contrast scan with a contrast injection timed according to an AIF curve and a VOF curve each estimated based on a prior contrast injection, according to an embodiment of the disclosure.
Figure 10:
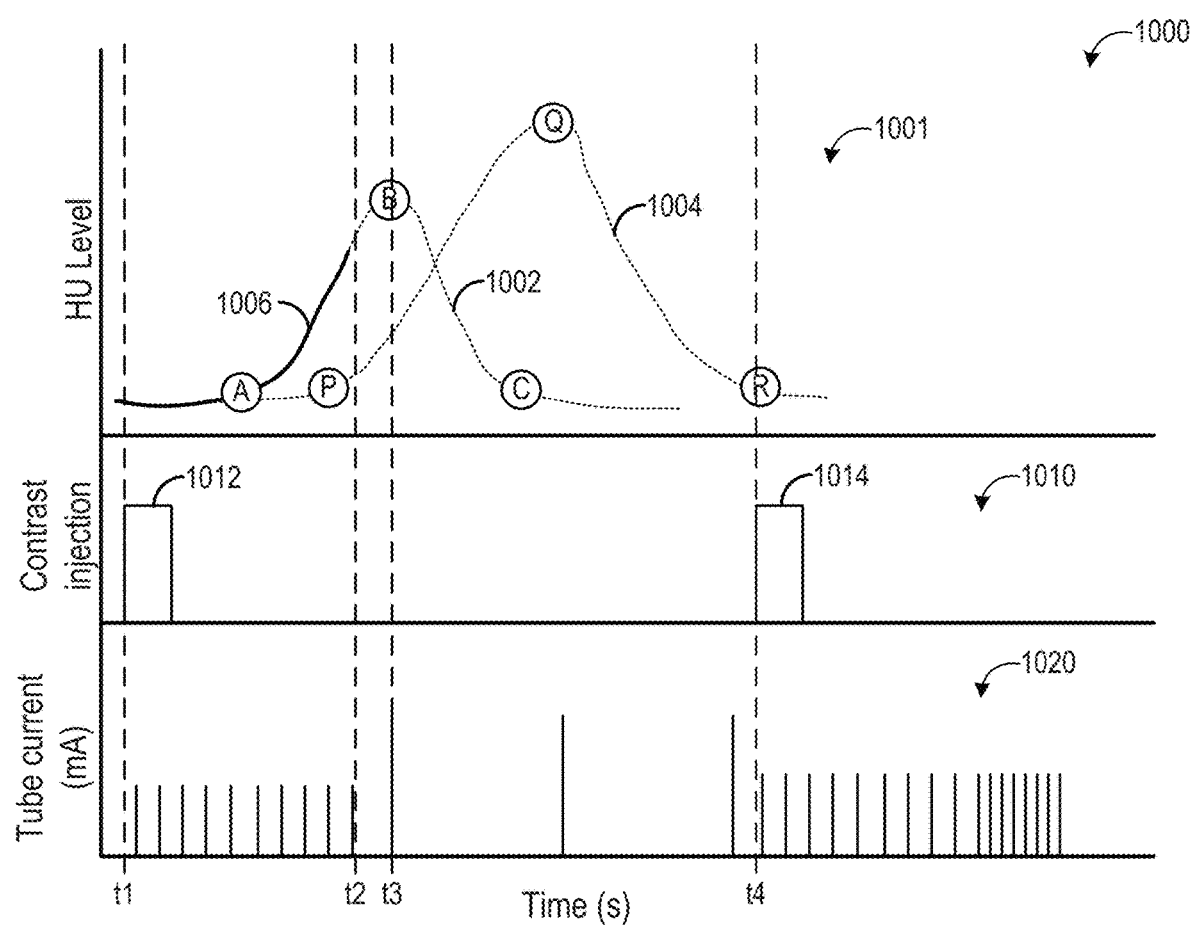
FIG. 10 is a timeline illustrating monitored contrast level at a monitoring region of interest (ROI), contrast injection events, and imaging events across two contrast scans carried out according to the method of FIG. 9.

A method for adaptive scan control, such as the method shown in FIG. 9, may include measuring the AIF or TUC signal for a patient from a first contrast bolus, determining the timing of the patient's venous return to baseline (VRTB) from the AIF or TUC signal via a model, and triggering administration of a second contrast bolus at the VRTB. Such a method enables personalization of the administration of the second contrast bolus on a patient-by-patient basis. FIG. 10 shows a timeline of contrast agent injections, CT scan acquisitions, and estimated AIF and VOF curves for an example scan protocol carried out according to the method of FIG. 9.

Figure 11:
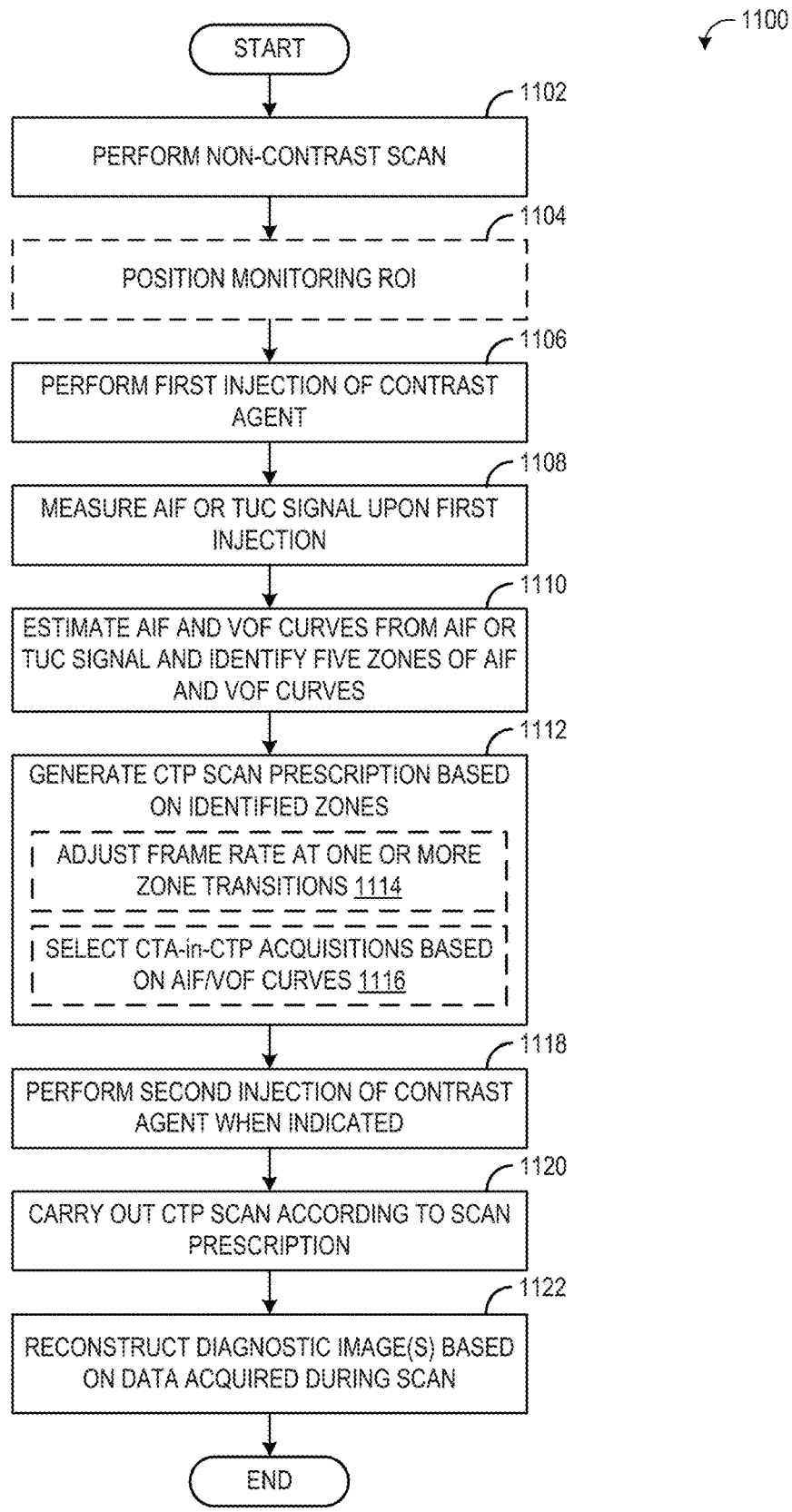
FIG. 11 is a flow chart illustrating a method for performing a personalized, five-zone perfusion scan, according to an embodiment of the disclosure.
Figure 12A:
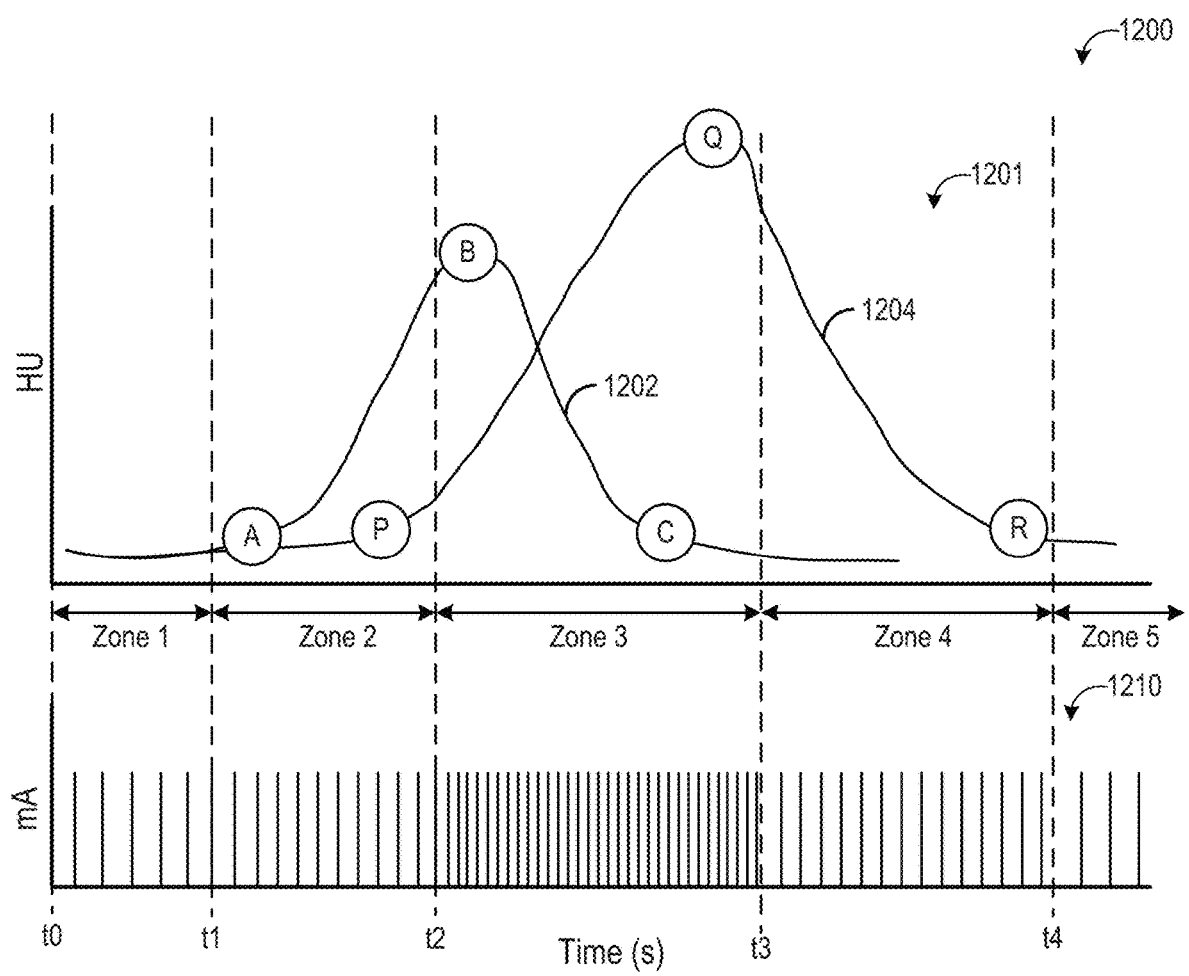
FIG. 12A is a timeline illustrating monitored contrast level at two monitoring ROIs and imaging events across a perfusion scan carried out according to the method of FIG. 11.
Figure 12B:
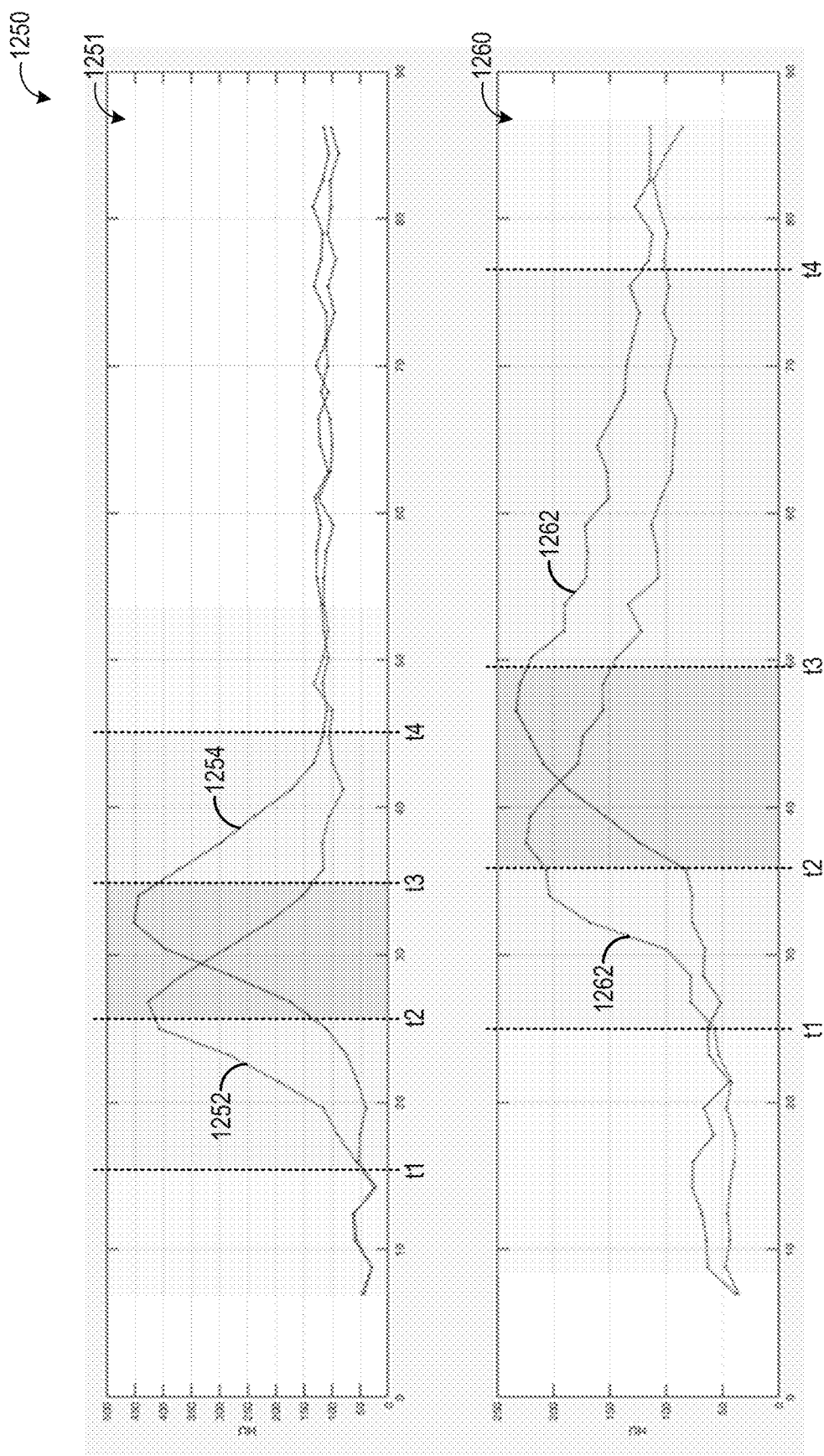
FIG. 12B shows plots of AIF and VOF curves and corresponding CTP scan zones for two example patients, determined according to the method of FIG. 11.

Another method for adaptive scan control, such as the method shown in FIG. 11, may include measuring the AIF or TUC signal for a patient from a first contrast bolus, determining the timing of a plurality of zone transitions for a CTP scan from the AIF or TUC signal via a model, and carrying out the CTP with a scan prescription that is determined based on the plurality of zone transitions. Such a method enables personalization of when certain changes to scan parameters (e.g., frame rate) are executed. FIG. 12A shows a timeline of CT scan acquisitions and estimated AIF and VOF curves for an example five zone CTP scan protocol, while FIG. 12B shows estimated AIF and VOF curves and corresponding zones of a CTP scan prescription for two example patients, each carried out according to the method of FIG. 11.

Figure 13:
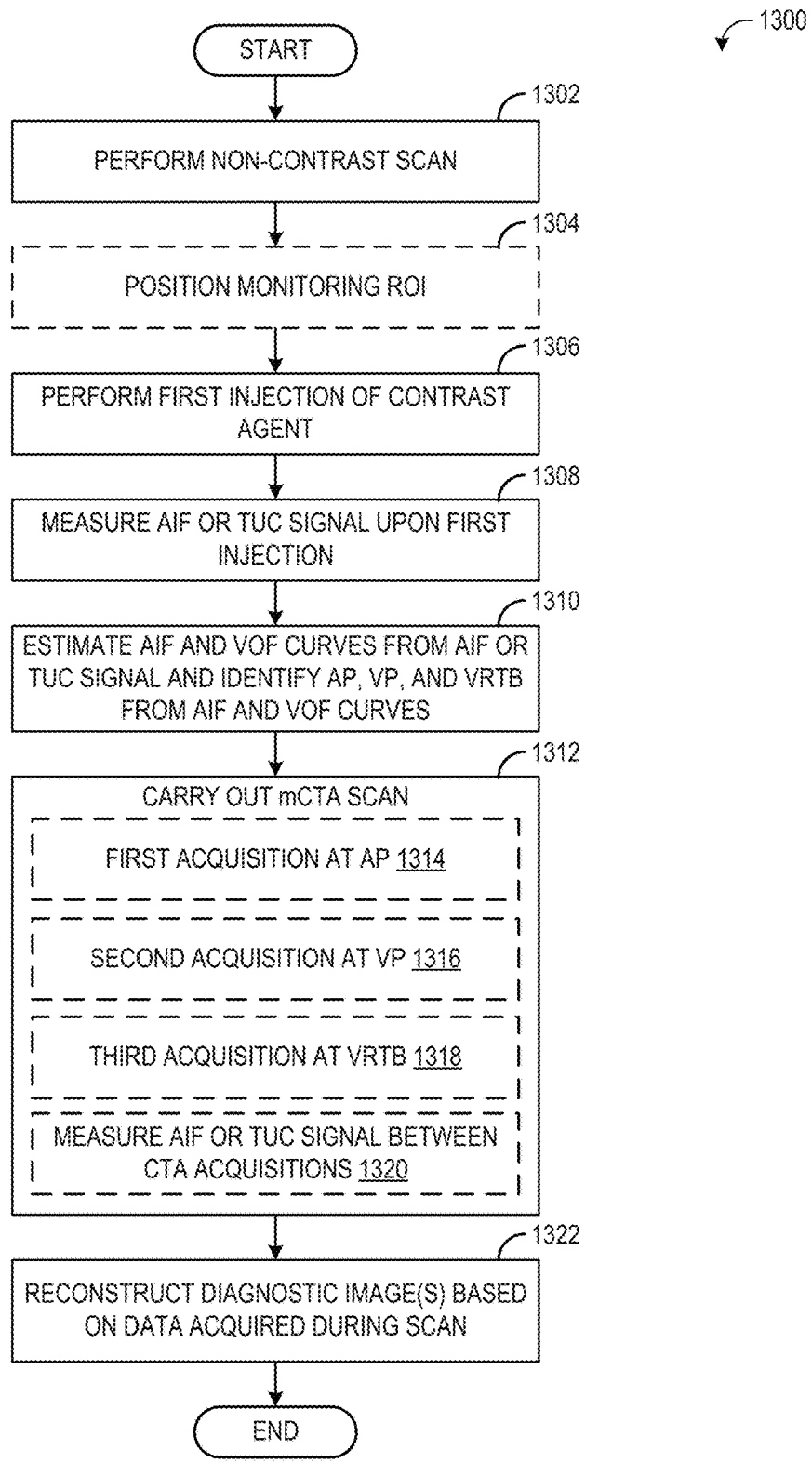
FIG. 13 is a flow chart illustrating a method for performing a personalized, multi-phase angiography scan, according to an embodiment of the disclosure.
Figure 14:
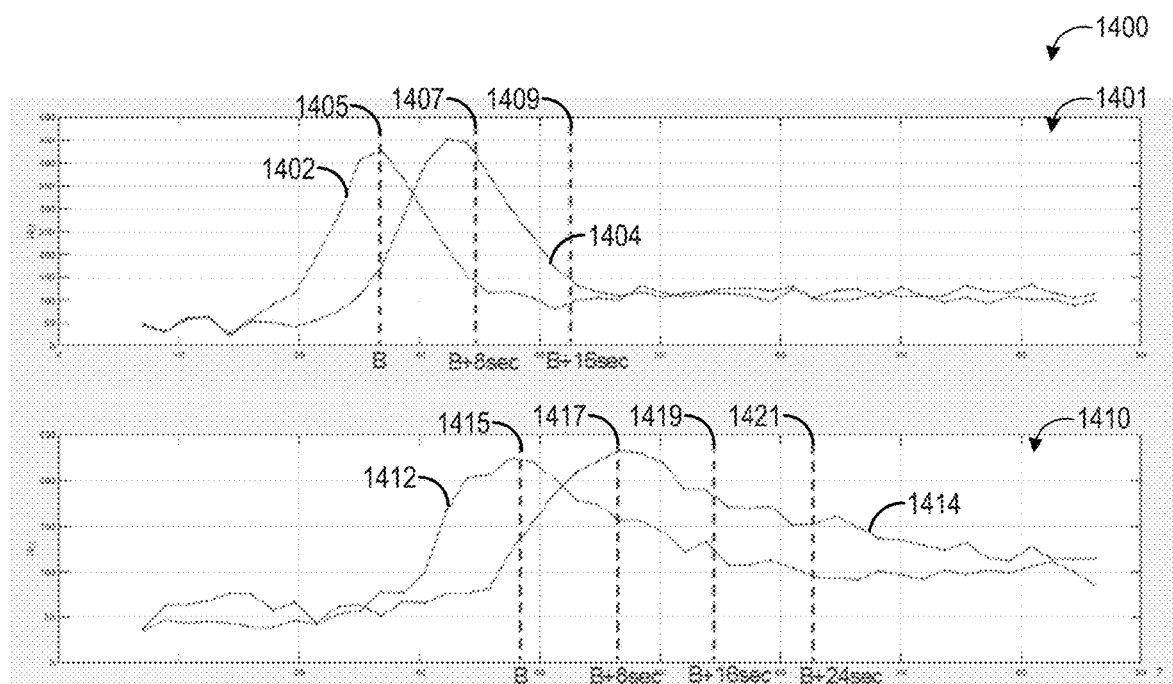
FIG. 14 is a graph depicting AIF and VOF curves for two example patients with angiography scan acquisitions timed according to a fixed time scan protocol.
Figure 15:
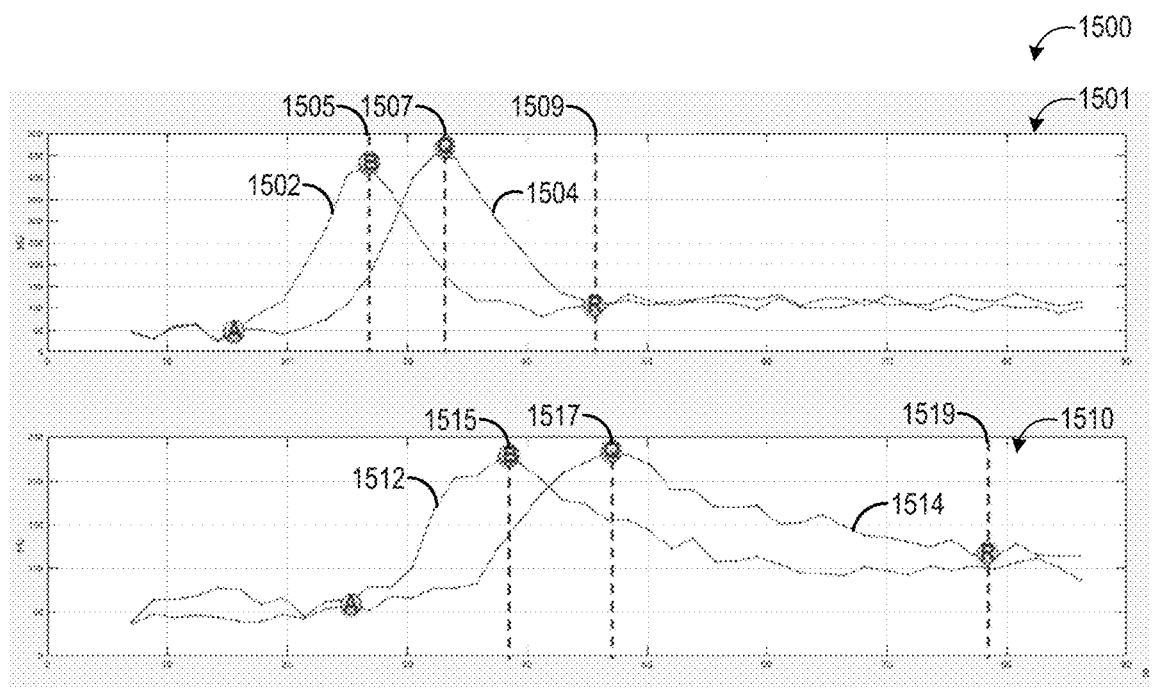
FIG. 15 is a graph depicting AIF and VOF curves for two example patients with angiography scan acquisitions timed according to the method of FIG. 13.

Another method for adaptive scan control, such as the method shown in FIG. 13, may include measuring the AIF or TUC signal for a patient from a first contrast bolus, determining the timing of a plurality acquisitions for a CTA scan from the AIF or TUC signal via a model, and carrying out the CTA scan with the acquisitions at the determined timing. Such a method enables personalization of when the CTA acquisitions are carried out to optimally acquire diagnostic images. FIG. 14 shows a timeline of CT scan acquisitions and estimated AIF and VOF curves for two patients using a fixed-timing CTA protocol and FIG. 15 shows a timeline of CT scan acquisitions and AIF and VOF curves for the two patients carried out according to the method of FIG. 13.

Figure 16:
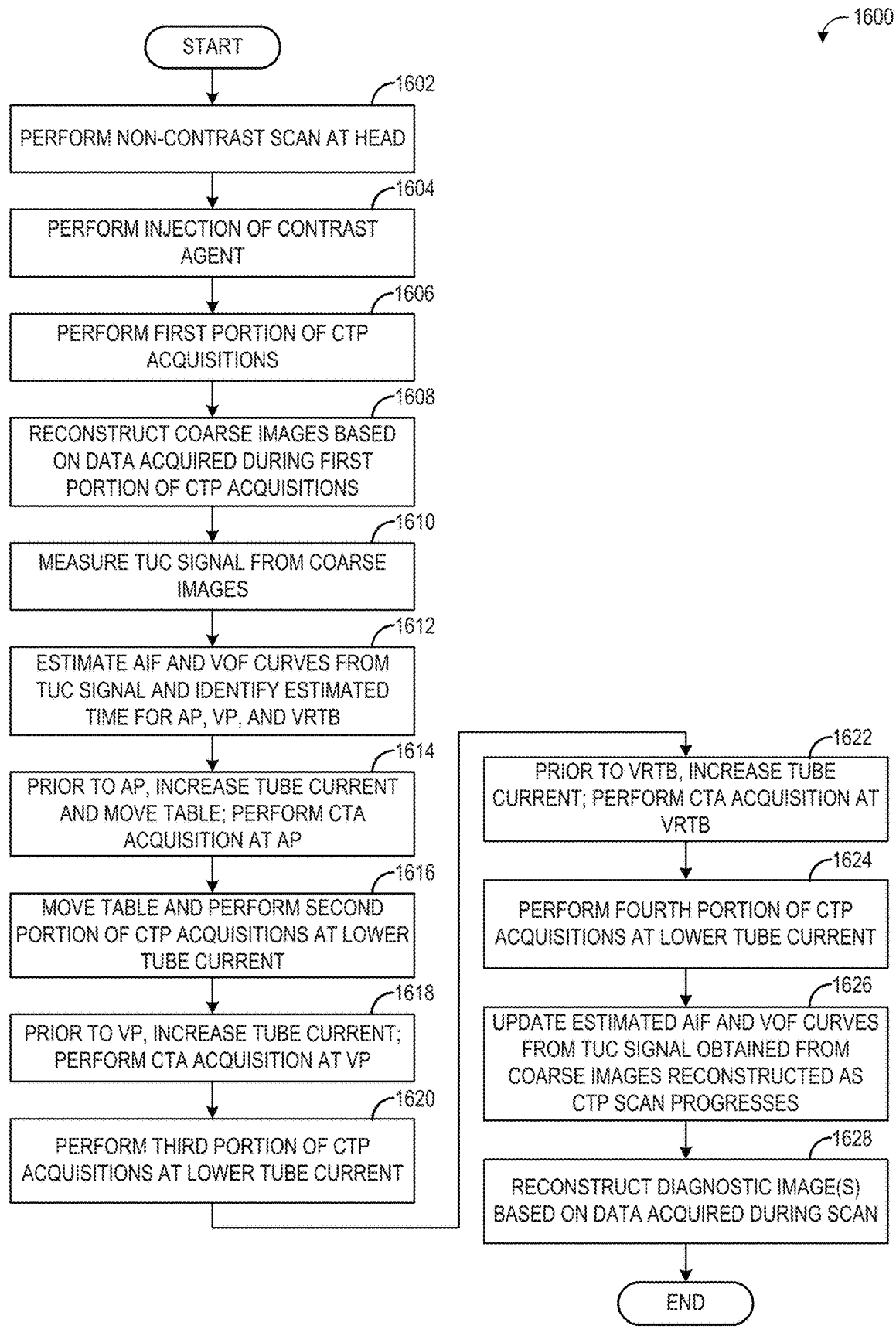
FIG. 16 is a flow chart illustrating a method for performing a personalized, multi-phase angiography scan within a perfusion scan, according to an embodiment of the disclosure.
Figure 17:
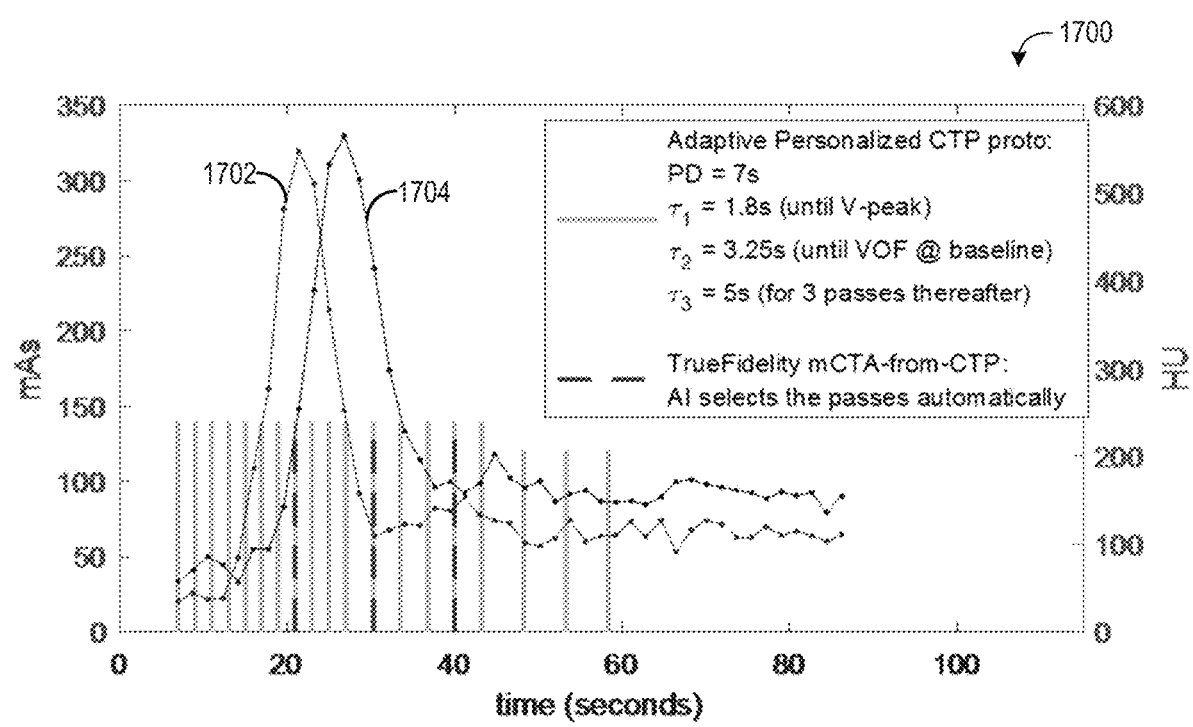
FIG. 17 is a graph depicting AIF and VOF curves for an example patient with perfusion and angiography scan acquisitions timed according to the method of FIG. 16.

Another method for adaptive scan control, such as the method shown in FIG. 16, may include measuring a TUC signal for a patient from a contrast bolus, determining the timing of a plurality acquisitions for a CTA scan from the TUC signal via a model, and carrying out the CTA scan with the acquisitions at the determined timing while also carrying out a CTP scan, without administering another contrast bolus. Such a method enables personalization of when the CTA acquisitions are carried out to optimally acquire diagnostic images. FIG. 17 shows a timeline of CT scan acquisitions and estimated AIF and VOF curves for a patient according to the method of FIG. 16.

Figure 18:
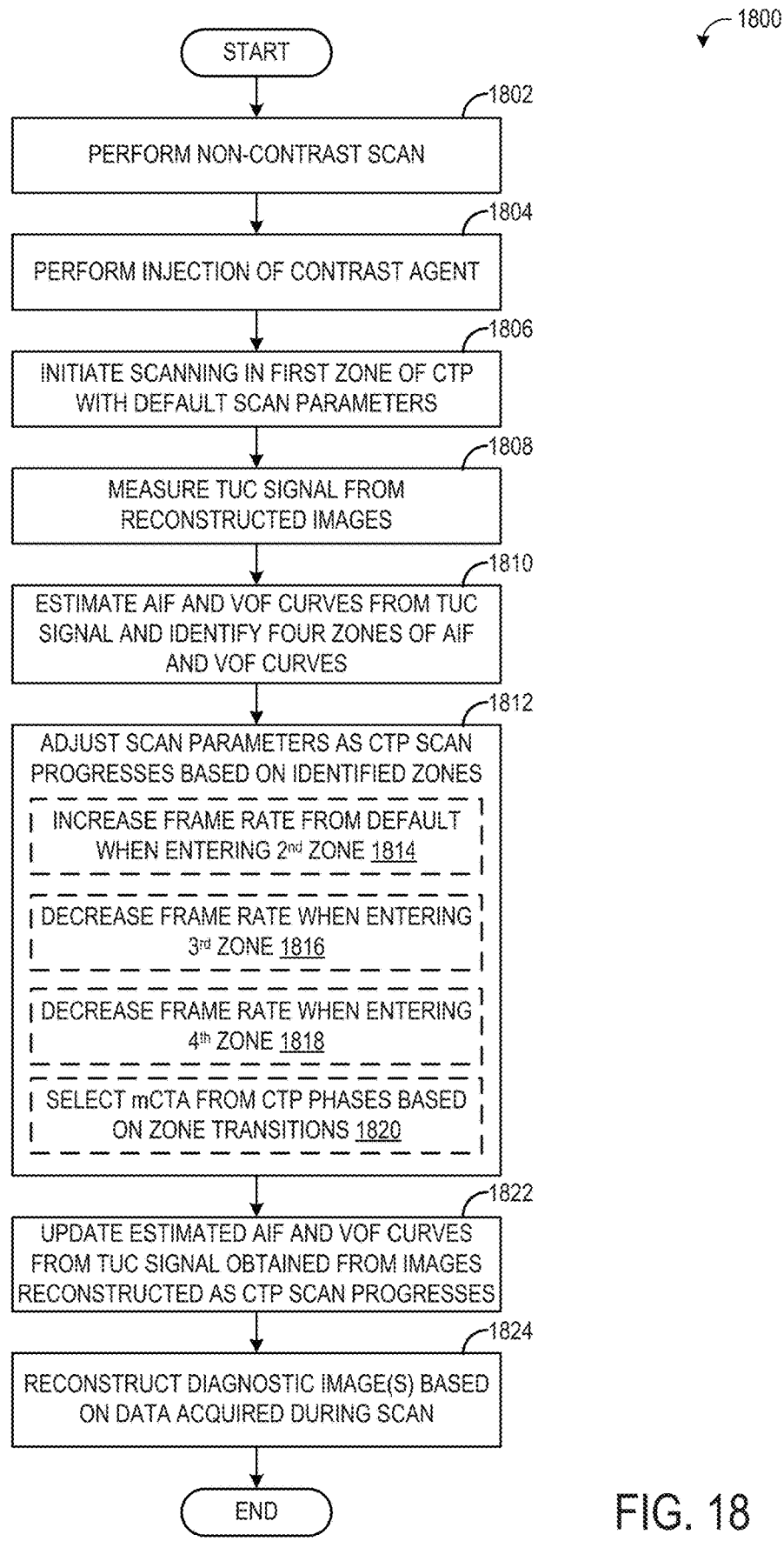
FIG. 18 is a flow chart illustrating a method for performing a personalized, four-zone perfusion scan, according to an embodiment of the disclosure.
Figure 19:
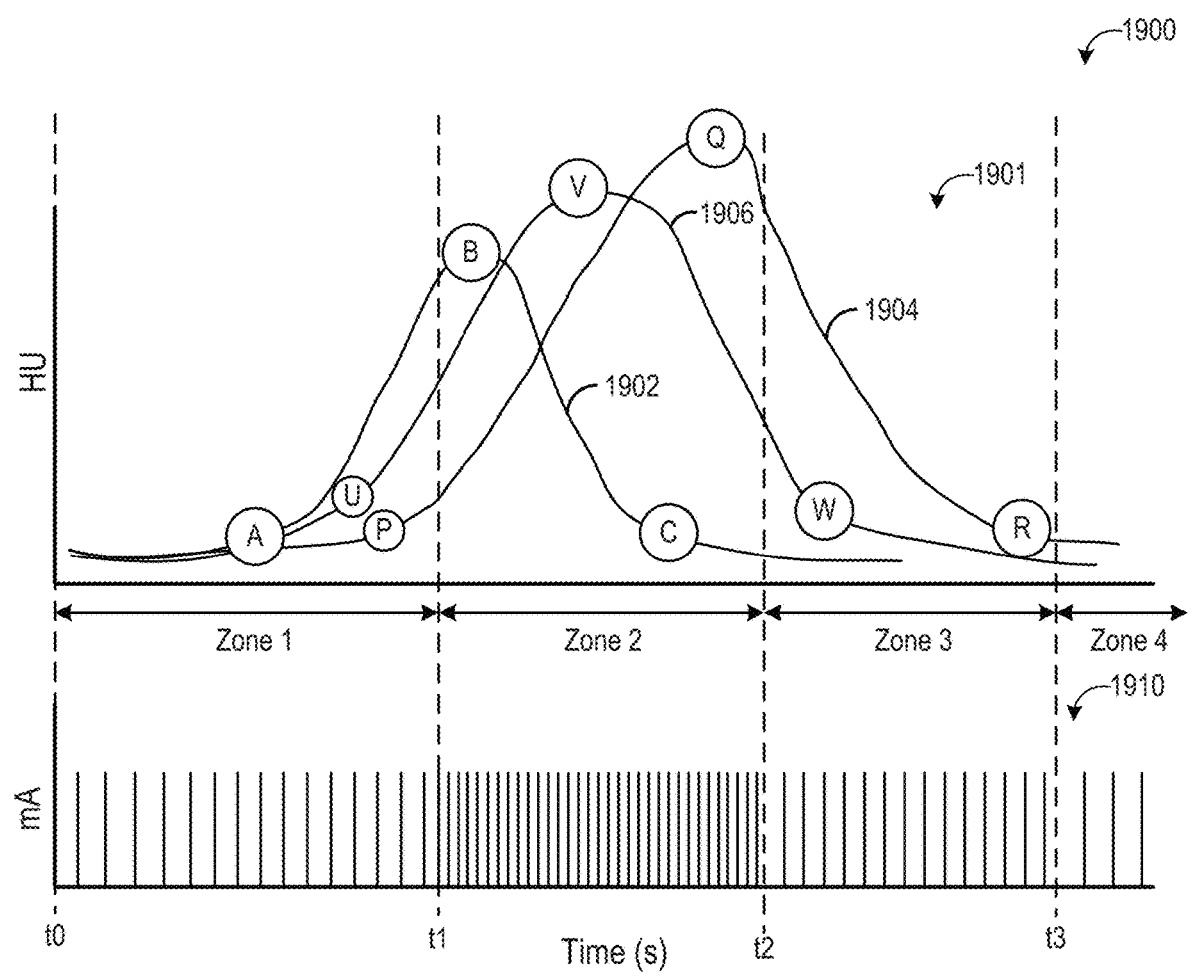
FIG. 19 is a graph depicting an AIF curve, a VOF curve, and a TUC for an example patient with perfusion scan acquisitions timed according to the method of FIG. 18.

Another method for adaptive scan control, such as the method shown in FIG. 18, may include measuring the TUC signal for a patient from a contrast bolus, determining the timing of a plurality of zone transitions for a CTP scan from the TUC signal via a model, and carrying out the CTP with a scan prescription that is determined based on the plurality of zone transitions, without administering another contrast bolus. Such a method enables personalization of when certain changes to scan parameters (e.g., frame rate) are executed. FIG. 19 shows a timeline of CT scan acquisitions and estimated AIF and VOF curves and a TUC for an example four zone CTP scan protocol carried out according to the method of FIG. 18.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detector elements are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, e.g., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may be a motorized table. Specifically, the table motor controller 226 may move the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the method described below with reference to FIG. 9) described further herein may be stored as executable instructions in non-transitory memory on a computing device (or controller) in imaging system 200. In an embodiment, computing device 216 may include the instructions in non-transitory memory, and may apply the methods described herein, at least in part, to measure the AIF or TUC signals from a plurality of reconstructed images after receiving the reconstructed images from image reconstructor 230. The computing device 216 may then enter the AIF or TUC signal to a model to estimate the AIF and VOF curves, as described below, in order to optimally time administration of a second contrast agent, plan personalized contrast scan prescriptions, and so forth, as described below. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display 232 allows the operator to evaluate the imaged anatomy, view measured and/or estimated AIF and VOF curves, trigger aspects of the contrast scans, and the like. The display 232 may also allow the operator to select a region of interest (ROI) and/or request patient information, for example, via a graphical user interface (GUI) for a subsequent scan or processing.

FIG. 3 shows a graph 300 depicting an example AIF curve 302 and an example VOF curve 304 each plotted as HU as a function of time. AIF curve 302 represents the change in the arterial inflow of a contrast agent over time for a patient, and VOF curve 304 represents the change in the venous outflow of the contrast agent over time for the patient. The AIF curve 302 may be measured at an arterial ROI, such as anterior cerebral artery or internal carotid artery, and may include a measurement of signal intensity in the arterial ROI relative to a baseline intensity (e.g., in the arterial ROI prior to contrast injection). The VOF curve 304 may be measured at a venous ROI, such as the superior sagittal sinus, and may include a measurement of the signal intensity in the venous ROI relative to a baseline intensity (e.g., in the venous ROI prior to contrast injection).

The AIF curve 302 may include an arterial ascent knee at approximately point A on the curve, an arterial peak at point B on the curve, and an arterial decent knee at approximately point C on the curve. The amount of time from contrast injection until the arterial peak is reached may be the time to arterial peak, indicated as t_AP on FIG. 3. The VOF curve 304 may include a venous ascent knee at approximately point P on the curve, a venous peak at point Q on the curve, and a venous decent knee at approximately point R on the curve. The amount of time from contrast injection until the venous peak is reached may be the time to venous peak, indicated as t_VP on FIG. 3. The amount of time from contrast injection until the venous return to baseline (VRTB) is reached may be the time to VRTB, indicated as t_VRTB on FIG. 3.

The amount of time it may take to reach the points marked on the curves in FIG. 3 may vary from patient to patient, as body weight, cardiac function, and other factors may impact the contrast agent inflow and outflow rate. As will be explained in more detail below, certain contrast scan protocols, such as perfusion and angiography scans, rely on the AIF and/or VOF curves, and the timing of one or more of the points described above (e.g., the arterial peak) may be determined and used as a trigger for commencing diagnostic imaging, adjusting scan parameters, and the like. However, some scan protocols are condensed as much as possible so that diagnostic information may learned as quickly as possible in order to facilitate patient care. For example, scan protocols carried out as part of an acute stroke assessment may be designed to be as short as possible, while still collecting the needed diagnostic image information, so that needed patient care may be administered as quickly as possible. Thus, the amount of time needed to completely measure both the AIF curve and the VOF curve for a patient prior to initiation of the diagnostic scan(s) may delay patient care and negatively impact patient outcomes. Further, when the imaging system includes x-rays directed to the patient (such as the CT system described above with respect to FIGS. 1-2), it may be desired to minimize patient radiation exposure. Thus, acute stroke and other contrast scan protocols may include a short measurement of the AIF curve, for example, and scan protocol adjustments may be based on this limited information and/or certain aspects of the scan protocols may be carried out with fixed timing that is not changed from patient to patient. While such protocols may be suitable for ensuring that most scans generate sufficient diagnostic information, some scans may result in images that are not suitable for diagnosing the patient condition or may lead to unnecessary radiation exposure.

Thus, prior to or during the beginning of a contrast scan, a small segment of the AIF curve may be measured and this AIF curve measurement (referred to as an AIF signal) may be used to estimate the remainder of the AIF curve as well as the VOF curve. To ensure an accurate estimation, a machine learning model may be deployed that is trained using a plurality of different AIF signals measured from different patients along with associated full AIF and VOF curves (or associated points of interest on the AIF and VOF curves, such as the points labeled on FIG. 3 and described above). The measured AIF signal may be entered into the trained and validated machine learning model, and the model may output an estimated AIF curve and estimated VOF curve, or the model may output the time to one or more significant points of the AIF and VOF curves, such as the time to arterial peak, the time to venous peak, and the time to venous return to baseline. The scan protocols may then be adapted on the fly on a patient by patient basis using the estimated AIF and VOF curves and/or estimated time points of the AIF and VOF curves.

FIG. 4 shows a graph 400 depicting an estimated AIF curve 402 and estimated VOF curve 404 each estimated according to a first estimation method, referred to as an augmented timing bolus (aTB) estimation. A timing bolus may include a small amount of contrast agent that is administered before a contrast scan is initiated. The inflow of the contrast agent of the timing bolus may be monitored and used to set parameters for the follow-on contrast scan. As shown, a first segment 406 of the AIF curve is measured as described above (e.g., in a ROI based on change in HU level relative to a baseline level). The first segment 406 may commence when the timing bolus is administered (e.g., at time t1 in FIG. 4) and end after the arterial peak (e.g., at time t2 in FIG. 4). The first segment 406 may be entered into a model to estimate the remaining portion of the estimated AIF curve 402 and all of the estimated VOF curve 404. As a result, time points A and B are measured while time points P', C', Q', and R' are estimated. In some examples, the first segment 406 may extend beyond what is shown in FIG. 4. For example, rather than terminating the measurement of the AIF curve at time t2, the measurement may extend until another suitable, later time. As the first segment is lengthened, the accuracy of the estimation of the subsequent time points may be increased, but extending the measurement period may increase the radiation dosage to the patient.

FIG. 5 shows a graph 500 depicting an estimated AIF curve 502 and estimated VOF curve 504 each estimated according to a second estimation method, referred to as an augmented smart prep (aSP) estimation. Smart prep may refer to an in-flight AIF measurement that occurs using the same contrast agent bolus that is administered for the contrast scan. The inflow of the contrast agent of the contrast scan bolus may be monitored and used to set parameters for the in-flight contrast scan. As shown, a first segment 506 of the AIF curve is measured (as described above). The first segment 506 may commence when the contrast bolus is administered (e.g., at time t1 in FIG. 5) and end before the arterial peak (e.g., at time t2 in FIG. 5), while arterial contrast enhancement is still increasing. The first segment 506 may be entered into a model to estimate the remaining portion of the estimated AIF curve 502 and all of the estimated VOF curve 504. As a result, time point A is measured while time points B', P'', C'', Q'', and R'' are estimated. Time points P'', C'', Q'', and R'' are given a double prime notation to indicate that the estimation of these time points may not be as accurate as the estimation of those time points using the aTB estimation method, given that the aSP estimation relies on less measured data than the aTB estimation.

Thus, the AIF and VOF curves (or selected time points of the AIF and VOF curves) may be estimated using a relatively short measured segment of the AIF curve that is entered into a machine learning model. The aTB estimation method, described with respect to FIG. 4, may result in a more accurate estimation of the AIF and VOF curves than the aSP estimation method, given the additional measured data that may be entered into the model. However, the aTB estimation method relies on a timing bolus or other separate contrast agent injection, and thus may be more time-consuming than the aSP estimation method.

While the aTB and aSP estimation methods were both described as being based on a single arterial ROI, it is to be understood that multiple arterial ROIs could be measured and combined (e.g., averaged) to measure the AIF curve. Further, the VOF curve could be measured for the same time period as the AIF curve (e.g., from time t1 until the respective time t2) by monitoring a venous ROI, and the measured segment of the VOF curve could be used as input to the model in addition to the measured segment of the AIF curve, which may result in a more robust estimation of the remaining portions of the AIF and VOF curves.

The arterial ROI and venous ROI described above may be positioned at any suitable location where arterial inflow and venous outflow, respectively, of contrast agent may be detectable, and the selection of where to position the arterial ROI and/or venous ROI may depend on the scan protocol (e.g., what anatomy is going to be imaged in the contrast scan). However, some anatomy, such as the brain, may present challenges for arterial or venous ROI placement, as the ability to visualize certain anatomical features may require presence of a contrast agent. Thus, to place an arterial or venous ROI in the head/brain, a separate administration of contrast agent may be needed to even place the ROI, which may make arterial or venous ROI placement in the head unpractical. Thus, the arterial ROI and/or venous ROI may typically be placed in the neck area or another adjacent anatomy, and then the patient may be moved relative to the CT imaging system (e.g., via table movement) to position the head in the proper location for the contrast scan. However, this additional table movement may prolong the duration of the scan session and/or make some adaptive scan protocols unpractical. Thus, as will be explained below, another method for estimating the AIF and VOF curves for use in adaptive scan protocols includes monitoring tissue uptake of contrast agent over an entire view/image rather than a small ROI.

FIG. 6 shows a graph 600 depicting an example AIF curve 602, an example VOF curve 604, and an example tissue uptake curve (TUC) 606 each plotted as HU as a function of time. AIF curve 602 and VOF curve 604 may be the same as AIF curve 302 and VOF curve 304 described above with respect to FIG. 3. TUC 606 may represent the change in detected contrast agent in a tissue of interest, as the contrast agent is taken up by the tissue and then depleted from the tissue. To measure the TUC, tissue of interest (e.g., the brain parenchyma) may be segmented in each of a plurality of reconstructed images, and the overall or average HU of in the segmented region of each of the plurality of reconstructed images may be determined relative to a baseline level and plotted over time. Additional details regarding the tissue segmentation and TUC signal measurement are provided below with respect to FIG. 16.

The AIF curve 602 may include the time points discussed above (e.g., A, B, and C) and the VOF curve 604 may include the time points discussed above (e.g., P, Q, and R). TUC 606 may include an ascent knee at approximately point U on the curve, a TUC peak at point V on the curve, and a decent knee at approximately point W on the curve. The timing of significant points are shown in FIG. 6, including t_AP, t_VP, and t_VRTB.

A segment of the TUC may be measured and then entered into a model to predict the AIF curve and the VOF curve, the remainder of the TUC, and/or time points of interest, similar to the aTB and aSP estimation methods described above. FIG. 7 shows a graph 700 depicting an estimated AIF curve 702, an estimated VOF curve 704, and an estimated TUC 706, each estimated according to a first TUC estimation method. The tissue uptake of a contrast agent (e.g., of a timing bolus) may be monitored and used to set parameters for the follow-on contrast scan. As shown, a first segment 708 of the TUC is measured as described above (e.g., a change in HU level relative to a baseline level measured across a plurality of images). The first segment 708 may commence when the timing bolus is administered (e.g., at time t1 in FIG. 7) and end after the TUC peak (e.g., at time t2 in FIG. 7). The first segment 708 may be entered into a model to estimate the remaining portion of the estimated TUC 706 and all of the estimated AIF curve 702 and VOF curve 704. As a result, time points U and V are measured while time points A', B', C', P', Q', and R' are estimated.

FIG. 8 shows a graph 800 depicting an estimated AIF curve 802, an estimated VOF curve 804, and an estimated TUC 806 each estimated according to a second TUC estimation method. The second TUC estimation method may be performed in-flight with a contrast scan, using the same contrast agent bolus that is administered for the contrast scan. The tissue uptake of the contrast agent may be monitored and used to set parameters for the in-flight contrast scan. As shown, a first segment 808 of the TUC curve is measured (as described above). The first segment 808 may commence when the contrast bolus is administered (e.g., at time t1 in FIG. 8) and end before the TUC peak (e.g., at time t2 in FIG. 8), while tissue uptake is still increasing. The first segment 808 may be entered into a model to estimate the remaining portion of the TUC 806 and all of the estimated AIF curve 802 and all of the estimated VOF curve 804. As a result, time point U is measured while time points A", B", V', W", P", C", Q", and R" are estimated. Time points with a double prime notation indicate that the estimation of these time points may not be as accurate as the estimation of those time points using the first TUC estimation method, given that the second TUC estimation relies on less measured data than the first TUC estimation.

Thus, the AIF, TUC, and VOF curves (or selected time points of the AIF, TUC, and VOF curves) may be estimated using a relatively short measured segment of the TUC that is entered into a machine learning model. The first TUC estimation method, described with respect to FIG. 7, may result in a more accurate estimation of the AIF and VOF curves than the second TUC estimation method described with respect to FIG. 8, given the additional measured data that may be entered into the model. However, the first TUC estimation method may rely on a timing bolus or other separate contrast agent injection, and thus may be more time-consuming than the second TUC estimation method.

FIG. 9 is a flow chart illustrating a method for timing a second contrast agent injection based on patient-specific contrast agent timing parameters determined from a first contrast agent injection. Method 900 is described with respect to the system and components described above with respect to FIGS. 1-2 but could be carried out with other systems/components without departing from the scope of this disclosure. Method 900 may be carried out according to instructions stored in non-transitory memory of a computing device (e.g., computing device 216 of FIG. 2). Method 900 may include a determination of a target timing for initiating injection of a contrast agent for a second contrast scan following a first contrast scan, or otherwise determining the target timing of a contrast agent injection where contrast agent contamination from a prior injection of contrast agent (e.g., a timing bolus) may confound accurate diagnosis of a patient condition. Thus, method 900 may be performed in response to user selection of a scanning protocol that includes two contrast scans performed in rapid succession, such as a CTA followed by a CTP or a CTP followed by a CTA, or in response to user selection of a scanning protocol that includes a timing bolus of contrast agent followed by a contrast scan, such as a CTP.

At 902, a non-contrast scan is optionally performed. The non-contrast scan may be taken to establish a baseline image for the area to be monitored before delivery of a contrast agent. The baseline image may then be used to align the patient and the region of interest within the imaging device. At 904, a monitoring region of interest (ROI) for contrast monitoring is optionally identified/positioned. The monitoring ROI may comprise a specific region of the patient wherein contrast level is monitored during the scan. In some examples, the monitoring ROI may be positioned outside of the area of the patient to be imaged. In other examples, the monitoring ROI may be positioned within the imaging area such that the projection data acquired for diagnostic purposes may also be used for monitoring. Thus, an operator may select the monitoring ROI based on the baseline image acquired at 902. Determining the monitoring ROI may therefore comprise receiving a selection of a monitoring ROI from an operator, for example via operator console 220. In some examples, a monitoring ROI may be not be identified/positioned. Rather, the monitoring ROI may be segmented tissue from a plurality of reconstructed images (e.g., when the tissue uptake curve signal is used to estimate the AIF/VOF curves and/or time points of interest).

At 906, a first injection of contrast agent into the patient is performed. As a non-limiting example, the contrast agent may comprise iodine. As other examples, the contrast agent may comprise an ionic contrast medium such as meglu-camine diatriozoate, or a non-ionic contrast medium such as iopromide or ohexol. The contrast agent may be intravenously injected using either automatic or manual methods. At 908, an arterial inflow function (AIF) or tissue uptake curve (TUC) signal is measured upon the first injection. As explained above with respect to FIGS. 3-6, the AIF signal may include a first portion of an AIF curve that is measured at an arterial ROI. Depending on the scanning protocol, the AIF segment may include and extend past the arterial peak (when the first contrast agent injection is a timing bolus), as shown in FIG. 4, or the AIF segment may not include the arterial peak (when the first contrast agent injection is the contrast agent injection for the first contrast scan), as shown in FIG. 5. Likewise, depending on the scanning protocol, the TUC segment may include and extend past the tissue uptake peak (when the first contrast agent injection is a timing bolus), as shown in FIG. 7, or the TUC segment may not include the tissue uptake peak (when the first contrast agent injection is the contrast agent injection for the first contrast scan), as shown in FIG. 8. To measure the AIF signal or the TUC signal, a plurality of images of the monitoring ROI may be reconstructed (e.g., by image reconstructor 230) from projection data obtained by the CT system (e.g., from projection data obtained via detector array 108, which detects x-rays generated by x-ray source 104) with a relatively low x-ray dose (e.g., a tube current of 100 mAs or less). When the AIF signal is obtained, the monitoring ROI may be an artery, and when the TUC signal is obtained, the monitoring ROI may be the entire brain (although the entire head region may be imaged, and the brain may be segmented from background/other tissue after image reconstruction). The signal intensity (e.g., in HU) of the monitoring ROI/segmented tissue relative to a baseline level for each image may be determined and plotted as a function of time to arrive at the AIF signal or TUC signal. In some examples, the AIF signal may be measured from raw projection data without requiring image reconstruction to measure the AIF signal.

The AIF signal or TUC signal may be measured for a period of time that is based on the scan protocol and patient-specific contrast uptake parameters. For example, when the first contrast injection is a timing bolus, the AIF signal or TUC signal may be measured for a first, longer period of time. In such examples, the AIF signal may be measured until just after the arterial peak is reached. The rate of change in contrast level (e.g., an instantaneous rate of change or the slope of the AIF curve) may be monitored to determine when the arterial peak has been reached. For example, a positive rate of change indicates that the contrast level is increasing, while a negative rate of change indicates that the contrast level is decreasing. Once a negative rate of change is indicated for at least two successive samples (e.g., scan acquisitions) following a positive rate of change indication for at least two successive samples (e.g., scan acquisitions) during measurement of the AIF signal, it may be confirmed that the arterial peak has been reached and the measurement may be terminated. Likewise, for the TUC signal, once a negative rate of change is indicated for at least two successive samples (e.g., scan acquisitions) following a positive rate of change for at least two successive samples during measurement of the TUC signal, it may be confirmed that the tissue uptake peak has been reached and the measurement may be terminated. When the first contrast injection is the contrast injection for the first contrast scan, the AIF signal or the TUC signal may be measured for a second, shorter period of time. In such examples, the AIF signal or TUC signal may be measured until a mid-point of the arterial contrast enhancement or a mid-point of the tissue contrast enhancement, respectively, such as until a specified number of measurement samples having a positive rate of change of contrast levels has been detected and/or until the first contrast scan is initiated by an operator of the imaging system.

At 910, a time at which the venous return to baseline (VRTB) of the first contrast injection occurs is estimated based on the AIF or TUC signal. Estimating the timing of the VRTB may include estimating the AIF and VOF curves from the AIF or TUC signal using a machine learning model, as indicated at 912. As explained above, the AIF or TUC signal may include a measured segment of the AIF curve or the TUC that may be used as input to a model, and the model may output the estimated AIF curve and the estimated VOF curve. The model may be a suitable machine learning model, such as a decision tree, regression model, neural network, and so forth. The regression model may include a bootstrap algorithm that is trained with a dataset of N samples, where each sample includes a measured signal (whether entire AIF and VOF curves, or select features such as rate of change at the ascent of the AIF curve, AIF peak time and height, and/or AIF knee time and height) from a respective patient and identified (e.g., by an expert) ground truth, such as HU and time values for certain points of interest on the AIV and/or VOF curves (e.g., A, B, C, Q, R), such that a plurality of measured signals and corresponding ground truths from a plurality of different patients are included in the dataset. The bootstrap algorithm creates random sub-samples of the dataset with replacement to output multiple values of a desired statistic, such as a mean. The average of those multiple values provides a robust estimate of the statistic. For example, the bootstrap algorithm may be applied to determine multiple values of each of a mean time to arterial peak, a mean time to venous peak, and a mean time to venous return to baseline, with each mean value correlated to an input measured signal. In some examples, the bootstrap algorithm may be aggregated where predictions (e.g., of the means described above) from multiple decision trees may be combined to reduce variance and overfitting. Cross-validation may be performed, where the input data (e.g., training dataset) is divided into n subsets, the regression model is trained with n−1 subsets, and the remaining subset is used to test the model to avoid overfitting.

In another example, the model may be a neural network that includes artificial neurons (referred to as units or nodes) arranged in a series of layers. The input units of the neural network receive information (e.g., the AIF or TUC signal), hidden units of the network process the information, the processed information is connected on positive or negative weights, and output units of the network signal a response to the learned information. In some examples, prior knowledge is used to reduce variance and improve generalizations and training data is run through the network and used to continuously change the weight vector of the network in response to a cost function, which improves the probability of an accurate output. In other words, the neural network may comprise a plurality of nodes/layers, including an input layer that receives the AIF or TUC signal and an output layer that outputs an estimated AIF curve and an estimated VOF curve (or estimated time to arterial peak, time to venous peak, and time to venous return to baseline), with connections/weights of the layers/nodes determined based on a training dataset. The training dataset may include a plurality of pairs of data, with each pair of data including measured AIF and VOF curves and an associated AIF or TUC signal, or with each pair of data including an AIF or TUC signal and corresponding time points of interest for a plurality of patients (e.g., t_AP, t_VP, and t_VRTB).

Estimating the timing of the VRTB may include identifying the VRTB from the VOF curve (e.g., estimated according to the machine learning model described above), as indicated at 914. For example, the VRTB may be identified as the point on the VOF curve where the contrast level drops back below a threshold, or where the VOF curve slope switches from a negative rate of change to no change. In still other examples, the model may output the timing of the VRTB (e.g., in addition to or instead of the VOF curve). The timing of the VRTB may include a duration (e.g., in seconds) from when the first contrast injection was performed until the VRTB is estimated to occur.

At 916, the first contrast scan is initiated. In some examples, the first contrast scan may be a CTP scan and the first contrast injection may be a timing bolus for the CTP scan. Thus, as indicated at 918, initiating the first contrast scan may include performing a second injection of contrast agent at the estimated time of the VRTB of the first contrast injection. The second contrast injection may be performed automatically (e.g., in response to a command from computing device 216 and without operator action) or the second contrast injection may be performed manually (e.g., by a clinician). When the injection is performed manually, a notification may be output (e.g., on display device 232) instructing the clinician of the target time to initiate the second contrast injection. For example, the notification may include a countdown timer that counts down (e.g. from one minute, from 30 seconds, etc.) to zero at which time the operator may commence the second contrast injection. Once the second contrast injection has started, scanning may be carried out (automatically or in response to an operator input requesting the scan commence) according to scan parameters dictated by the scan protocol. For example, the x-ray tube current may be increased and the table supporting the patient may be moved in order to position the patient at a location dictated by the scan protocol (if the monitoring ROI is outside the imaging area).

In other examples, the first contrast scan may be a CTA or other contrast scan that is performed in-flight with the first contrast scan injection, as indicated at 920. In such examples, the first contrast scan may be initiated in response to operator input requesting scanning commence or automatically in response to the measured AIF or TUC signal indicating that the arterial peak of contrast enhancement is about to be reached. In such examples, the first contrast scan may be initiated without an additional contrast injection. The scanning may be carried out according to scan parameters dictated by the scan protocol, e.g., tube current may be increased, the table may be moved, etc.

At 922, a second injection of contrast agent is optionally performed at the estimated time of VRTB for the first contrast injection. This second injection may be performed prior to a second contrast scan following the first contrast scan, such as a CTP following a CTA. In this way, the second contrast injection may be timed to start once the contrast agent from the first contrast injection has returned to baseline, thereby avoiding contrast agent contamination while reducing delayed commencement of the second contrast scan. However, in some examples, the second injection of contrast agent may be performed at a time other than the estimated VRTB, such as after the VRTB. For example, when tissue permeability surface is measured with CTP, the CTP acquisitions may continue to be performed past VRTB. Thus, in such examples, it may be preferable to delay the second injection of contrast agent until after VRTB, such as a point after VRTB that is determined as a function of the time to arterial peak, venous peak, and/or VRTB (e.g., a first harmonic of the arterial peak). As described above, the second contrast injection may be performed automatically (e.g., in response to a command from computing device 216 and without operator action) or the second contrast injection may be performed manually (e.g., by a clinician). When the injection is performed manually, a notification may be output (e.g., on display device 232) instructing the clinician of the target time to initiate the second contrast injection. At 924, the second contrast scan is optionally initiated (e.g., the CTP scan is initiated) automatically or in response to an operator input requesting the second contrast scan commence. The second contrast scan may be carried out according to scan parameters dictated by the scan protocol, and may include adjustments to tube current, table position, frame rate, or other parameters relative to the first contrast scan. In some examples, where two contrast scans are performed, the AIF curve and/or TUC may continue to be measured during the first contrast scan where possible. For example, if the first contrast scan is a multi-phase CTA, the monitoring ROI may be imaged between acquisitions of the mCTA during non-imaging periods of the scan protocol where the CT system may otherwise be inactive. In doing so, the estimation of the AIF/VOF curves and/or VRTB may be improved by allowing additional AIF signal to be obtained and input to the machine learning model. The second injection of contrast agent at 922 and the initiation of the second contrast scan may be optional in that they may only be performed during scan protocols where two contrast scans are performed. Otherwise, for example if only a single contrast scan is performed, method 900 may proceed directly to 926.

At 926, one or more diagnostic images are reconstructed based on data acquired during the contrast scan(s). For example, one or more diagnostic images may be reconstructed using known reconstruction techniques, such as filtered back projection or iterative reconstruction. When two contrast scans are carried out, images may be constructed for each scan, e.g., CTA images and CTP images. The one or more diagnostic images may be output to a display device (e.g., display device 232) for display to an operator or a physician, to a storage medium (e.g., mass storage 218) for retrieving at a later time, and so on. Method 900 may then end.

FIG. 10 shows an example timeline 1000 of a scan protocol that includes two contrast scans carried out according to the method 900 of FIG. 9. The example scan protocol depicted in timeline 1000 is an mCTA scan followed by a CTP scan. Timeline 1000 includes a first plot 1001 showing estimated contrast levels determined from an aSP estimation method. As such, plot 1001 includes an estimated AIF curve 1002, an estimated VOF curve 1004, and an AIF segment 1006 that is actually measured, as explained above with respect to FIG. 5. Plot 1010 shows contrast injection events and plot 1020 shows scanning passes (also referred to as acquisitions, with the tube current for each acquisition of the CT imaging system). As used herein, a scan acquisition or pass may refer to a full gantry rotation (e.g., when the brain is being imaged) or a partial gantry rotation (e.g., when the heart is being imaged). In either case, an acquisition or pass may include the amount of gantry rotation that is needed to obtain the desired views for the anatomy/scanning protocol. Each plot is a function of time and all plots are time aligned.

At time t1, a first contrast injection is started. At the same time, imaging at the monitoring ROI (e.g., an artery) begins, with low tube current and a suitable frame rate. For example, the AIF signal may be measured with a tube current of less than 100 mAs. The AIF signal may be measured based on the detected contrast levels of the images reconstructed from time t1 to time t2. The AIF signal may be the AIF segment 1006 shown in FIG. 10. At time t2, the operator (e.g., of the CT system) may determine that the arterial peak of the contrast injection is about to occur, and thus measurement of the AIF signal may stop and the first contrast scan may begin at time t3. The first contrast scan may be an mCTA and thus may include three passes of the CT imaging system at fixed intervals starting at time t3. For example, as shown, one pass may occur every eight seconds or other suitable time. The tube current during the first contrast scan may be higher than during the contrast level measurement period. The AIF signal obtained from time t1 to time t2 may be entered into a machine learning model, which may determine the estimated AIF and VOF curves shown in FIG. 10, or the machine learning model may determine the VRTB (point R). At the VRTB of the first contrast injection, at time t4, the second contrast injection begins and the CTP scan commences. The CTP scan may be performed at a lower tube current and higher frame rate than the mCTA scan. Further, the CTP scan may include different periods with different frame rates, and may extend beyond the time shown in FIG. 10.

Thus, the method described above with respect to FIG. 9 and the corresponding example timeline described with respect to FIG. 10 provide for timing an injection of a second contrast bolus based on patient-specific uptake and clearance of the contrast agent determined during a prior injection of a first contrast bolus, so that the injection of the second contrast bolus may be performed as soon as the contrast agent of the first contrast bolus has returned to baseline levels. The timing of the injection of the second contrast bolus is determined based on a contrast signal measured upon injection of the first contrast bolus, where the contrast signal includes a segment of an arterial inflow function curve (as shown in FIGS. 4 and 5) or a segment of a tissue uptake curve (as shown in FIGS. 7 and 8). The contrast signal is entered as input to a machine learning model that is trained to estimate the arterial inflow function curve, the tissue uptake curve, and/or a venous outflow function curve.

In other examples, additionally or alternatively, the machine learning model may be trained to estimate certain time points of interest based on the contrast signal, such as a time to an arterial peak of the arterial inflow function curve, a time to a tissue uptake peak of the tissue uptake curve, a time to a venous peak of the venous outflow function curve, and/or a time to a venous return to baseline of the venous outflow function curve. Based on the estimated AIF and VOF curves and/or the estimated time points of interest, the target timing for the injection of the second contrast bolus may be determined, e.g., the injection of the second contrast bolus may be performed at an estimated venous return to baseline of the first contrast bolus. As explained above, the first contrast bolus may be a timing bolus administered before a contrast scan (in which case the second contrast bolus may be administered as part of the contrast scan), or the first contrast bolus may be administered in-flight with a first contrast scan and the second contrast bolus may be administered as part of a second contrast scan.

In some examples, a contrast scan carried out according to the method of FIG. 9 may include a CT perfusion scan (referred to as a CTP scan). A CTP scan may produce diagnostic images showing blood profusion and delivery of blood or blood flow to a tissue of interest, such as a brain. A first example of a typical CTP protocol of the head may include a series of acquisitions performed at a single frame rate (e.g., one acquisition each 1.8 s) for a fixed duration (e.g., 87 s) following injection of a contrast bolus (assuming a prep delay between injection of the contrast bolus and the first acquisition of 5-7 s). In second example of a typical CTP protocol of the head, the acquisitions may be carried out at two different frame rates, for example a first frame rate (e.g., of one acquisition every 2 s) for a first duration (e.g., of 31 s) and then a second frame rate (e.g., of one acquisition every 5 s) for a second duration (e.g., of 35 s, for a total of 66 s) following injection of a contrast bolus (assuming a prep delay between injection of the contrast bolus and the first acquisition of 5-7 s). Ideally, a patient would be scanned at a higher frame rate during contrast enhancement (e.g., during the arterial and venous peaks) and scanning would end soon after the contrast agent returned to baseline. In the first example CTP protocol, the majority of patients, regardless of individual AIF and VOF curves, would be scanned such that diagnostic images are obtained, but some patients may be over-scanned. For example, patients with relatively short AIF/VOF peak times may be scanned for a relatively long duration after the contrast agent has returned to baseline, resulting in overly lengthy scan times and unnecessary radiation doses. In the second example CTP protocol, some patients (e.g., those with relatively long AIF/VOF peak times, such as older patients or patients with atrial fibrillation) may be under-scanned such that sufficient images as contrast is being washed out are not obtained, resulting in image quality issues (e.g., unreliable penumbra/blood flow quantitation, which may lead to an incorrect decision being made regarding whether the patient should receive an endovascular thrombectomy or other treatment). Thus, with typical CTP protocols, a tradeoff may be made between ensuring high quality images for all patients and increased exam time and corresponding increased radiation dose for some patients.

Thus, according to embodiments disclosed herein, an idealized, personalized "five-zone" CTP scan may be carried out based on the patient-specific contrast signal and output of the machine learning model described above (e.g., based on the estimated AIF and VOF curves). The CTP scan protocol may be divided into five zones, with each zone having specified scan parameters (e.g., frame rate, tube current, etc.). The times at which each zone transition (e.g., from one zone to the next zone) are to occur may be estimated using the machine learning model based with the measured contrast signal (e.g., measured from a prior contrast bolus injection) as input to the machine learning model. The scan prescription for the CTP scan (e.g., the CT system parameters for carrying out the scan) may be dynamically determined prior to execution of the CTP scan based on the timing of each zone transition, such that the CTP scan may be carried out in a manner that is optimized for the specific patient. In doing so, total scan time may be reduced, radiation exposure may be lowered, and image quality may be maintained.

FIG. 11 shows a flow chart illustrating a method 1100 for carrying out a personalized five-zone CTP scan. Method 1100 is described with respect to the system and components described above with respect to FIGS. 1-2 but could be carried out with other systems/components without departing from the scope of this disclosure. Method 1100 may be carried out according to instructions stored in non-transitory memory of a computing device (e.g., computing device 216 of FIG. 2). Method 1100 may include identification of estimated times of the transitions between five zones of a CTP scan, which may be used to determine a scan prescription for carrying out the CTP scan. Thus, method 1100 may be performed in response to user selection of a scanning protocol that includes a CTP, such as a stand-alone CTP, a CTA followed by a CTP, a CTP followed by a CTA, a combined CTP and CTA, etc.

At 1102, a non-contrast scan is optionally performed, as explained above with respect to FIG. 9. At 1104, a monitoring region of interest (ROI) for contrast monitoring is optionally identified/positioned, similar to the manner that the monitoring ROI was positioned in method 900 described above. At 1106, a first injection of contrast agent into the patient is performed, similar to the first injection of contrast agent described above with respect to FIG. 9 (e.g., the first injection may be a timing bolus or the first injection may be a contrast bolus for an in-flight contrast scan other than the CTP, such as a CTA performed before the CTP). At 1108, an AIF or TUC signal is measured at the monitoring ROI or segmented tissue upon the first injection. The AIF signal or TUC signal may be measured as explained above with respect to FIG. 9, and thus may include measurement of a first segment of the AIF curve (e.g., to either before the arterial peak as shown in FIG. 5 or until just after the arterial peak as shown in FIG. 4) or a measurement of a first segment of the TUC (e.g., until before the tissue uptake peak as shown in FIG. 8 or until just after the tissue uptake peak as shown in FIG. 7). To measure the AIF signal or the TUC signal, a plurality of images of the monitoring ROI may be reconstructed (e.g., by image reconstructor 230) from projection data obtained by the CT system (e.g., from projection data obtained via detector array 108, which detects x-rays generated by x-ray source 104) with a relatively low x-ray dose (e.g., a tube current of 50 mA or less). The signal intensity (e.g., in HU) of the monitoring ROI relative to a baseline level for each image may be determined and plotted as a function of time to arrive at the AIF signal or TUC signal.

At 1110, the AIF and VOF curves may be estimated based on the AIF or TUC signal. For example, as explained above with respect to FIG. 9, the AIF or TUC signal may be input into a machine learning model (e.g., a regression model, a neural network, or other suitable model), which may output the estimated AIF and VOF curves. In other examples, the machine learning model may output time points of interest, such as the arterial ascent knee (point A in FIG. 3), arterial peak (point B), and arterial decent knee (point C) of the AIF curve, and venous ascent knee (point P), venous peak (point Q), and venous return to baseline (point R) of the VOF curve, etc., based on the AIF or TUC signal. The five zones of the CTP scan may then be identified base on the estimated AIF and VOF curves and/or the estimated time points of interest.

As one example, the first zone may begin when the first injection of contrast agent begins or the first zone may begin after a predefined delay after the first injection has commenced. A first transition from the first zone to the second zone may be identified based on the timing of the arterial ascent knee. For example, the first transition from the first zone to the second zone may be estimated to occur two seconds before the arterial ascent knee (e.g., two seconds before time point A). A second transition from the second zone to the third zone may be identified based on the arterial peak (point B), for example, the second transition may be estimated to occur two seconds before the arterial peak. A third transition from the third zone to the fourth zone may be identified based on the venous peak (point Q), for example, the third transition may be estimated to occur two seconds after the venous peak. A fourth transition from the fourth zone to the fifth zone may be identified based on the venous return to baseline (VRTB, point R), for example, the fourth transition may be estimated to occur two seconds after the VRTB. The fifth zone may end at a fixed time after the VRTB, such as fourteen seconds after VRTB.

At 1112, a CTP scan prescription is generated based on the identified zones/zone transitions. For example, as explained above, values for one or more scan parameters may be adjusted for one or more zones, such as frame rate, tube current, tube voltage, etc., and thus the scan prescription may include instructions for when to adjust the values of the scan parameters. As an example, generating the scan prescription may include adjusting the frame rate of the CT system at one or more zone transitions, as indicated at 1114. In this way, some zones (e.g., the third zone) may have a higher frame rate than other zones (e.g., the fifth zone), and the transition from a lower frame rate to a higher frame rate or vice versa may be made when a selected zone transition is estimated to occur.

In some examples, a CTA may be performed along with the CTP, referred to as a CTA-in-CTP scan. In such examples, the timing of the CTA acquisitions may be selected based on the estimated AIF and VOF curves, as indicated at 1116. For example, the CTA acquisitions may be selected to occur at the arterial peak, venous peak, and VRTB. The CTA may be a "virtual" CTA where select CTP acquisitions may be used to reconstruct CTA images, and these select CTP acquisitions may be chosen based on the estimated AIF and VOF curves. For example, the estimated AIF, TUC, and/or VOF curves may be displayed with selectable points. A user may select the selectable points corresponding to the CTP acquisitions that are to be used for the CTA (e.g., acquisitions 4, 7, and 11) and instruct the system to generate TrueFidelity reconstructions of those acquisitions to generate a virtual head-only CTA from the CTP. In other examples, the CTA may be a multi-phase CTA (referred to as an mCTA) where a first head and neck acquisition is followed by two head-only acquisitions. The timing of these mCTA acquisitions may be selected based on the estimated AIF/VOF curves as described above, and the acquisitions may be performed at a different tube current than the CTP acquisitions, at least in some examples. When performing the mCTA in the CTP, the table may be moved in order to perform the first mCTA acquisition and then moved back to continue the CTP acquisitions. Additional details about carrying out an mCTA-in-CTP scan are provided below with respect to FIG. 16.

At 1118, a second injection of contrast agent is performed when indicated. In some examples, the second injection of contrast agent may be performed at the VRTB of the first injection of contrast agent, as explained above with respect to FIG. 9. At 1120, the CTP scan is carried out according to the scan prescription generated at 1112. Carrying out the CTP scan according the scan prescription may include commencing the CTP scan at the start of the first zone and scanning in the first zone at a first frame rate, first tube current, etc.; transitioning to the second zone at the first transition time (determined as explained above) and scanning in the second zone at a second frame rate, second tube current, etc.; transitioning to the third zone at the second transition time (determined as explained above) and scanning in the third zone at a third frame rate, third tube current, etc.; transitioning to the fourth zone at the third transition time (determined as explained above) and scanning in the fourth zone at a fourth frame rate, fourth tube current, etc.; and transitioning to the fifth zone at the fourth transition time (determined as explained above) and scanning in the fifth zone at a fifth frame rate, fifth tube current, etc. The scanning in the fifth zone may stop after a suitable number of acquisitions have been performed, such as three. In some examples, the first frame rate may be different than the second frame rate, the second frame rate may be different than the third frame rate, the third frame rate may be different than the fourth frame rate, and the fourth frame rate may be different than the fifth frame rate. In some examples, one or more of the zones may have the same frame rate. In some examples, one or more of the zones may have the same tube current and/or one or more of the zones may have different tube current. In some examples, carrying out the CTP scan may include performing the mCTA acquisitions at the times indicated in the scan prescription.

At 1122, one or more diagnostic images are reconstructed based on data acquired during the CTP scan. For example, one or more diagnostic images may be reconstructed using known reconstruction techniques, such as filtered back projection or iterative reconstruction. When two contrast scans are carried out, images may be constructed for each scan, e.g., CTA images and CTP images. The one or more diagnostic images may be output to a display device (e.g., display device 232) for display to an operator or a physician, to a storage medium (e.g., mass storage 218) for retrieving at a later time, and so on. Method 1100 may then end.

FIGS. 12A and 12B show example timelines of five zone, personalized CTP scans carried out according to the method of FIG. 11. Referring first to FIG. 12A, it illustrates a timeline 1200 that includes a first plot 1201 showing estimated contrast levels determined from an aTB estimation method, an aSP estimation method, or a TUC estimation method. As such, plot 1201 includes an estimated AIF curve 1202 and an estimated VOF curve 1204, as explained above with respect to FIGS. 3-8. Plot 1210 shows scanning events (with the x-ray tube current for each acquisition of the CT imaging system). Each plot is a function of time and the plots are time aligned. Dashed lines show time points of interest, herein the identified zone transitions.

The first zone (zone 1) may commence at time t0, which may correspond to the beginning of a contrast agent injection. After a prep delay (e.g., of 5 seconds), scanning may commence. In zone 1, the acquisitions may occur at a first frame rate, such as a frame rate of one acquisition every 5 seconds. The first transition may be estimated to occur at time t1, which may be two seconds before point A on the AIF curve 1202. When transitioning to the second zone (zone 2) at time t1, the acquisition frame rate may be increased, such that scanning occurs at a second frame rate in zone 2. In one example, the second frame rate may be one acquisition every 3 seconds. The second transition may be estimated to occur at time t2, which may be two seconds before point B on the AIF curve 1202. When transitioning to the third zone (zone 3) at time t2, the acquisition frame rate may be increased, such that scanning occurs at a third frame rate in zone 3. In one example, the third frame rate may be in a range of 1.5 s-2.8 s, such as one acquisition every 2 seconds. The third transition may be estimated to occur at time t3, which may be two seconds after point Q on the VOF curve 1204. When transitioning to the fourth zone (zone 4) at time t3, the acquisition frame rate may be decreased relative to the third zone, such that scanning occurs at a fourth frame rate in zone 4, which may be equal to the second frame rate in the example shown in FIG. 12A or another suitable frame rate (e.g., one acquisition every 4-5 seconds). The fourth transition may be estimated to occur at time t4, which may be two seconds after point R on the VOF curve 1204. When transitioning to the fifth zone (zone 5) at time t4, the acquisition frame rate may be decreased relative to the fourth zone, such that scanning occurs at a fifth frame rate in zone 5. In one example, the fifth frame rate may be one acquisition every 5-10 seconds. In some examples, only three acquisitions may occur in zone 5, and then the CTP scan may end. In the example scan sequence shown in FIG. 12A, the tube current and voltage may be kept constant between zones. However, in some examples, the tube current and/or voltage may change between zones, e.g., the tube current may be lowered for the fourth and fifth zones.

FIG. 12B shows example AIF/VOF curves and associated zones for five-zone CTP scans for two example patients, according to scan prescriptions determined via the method of FIG. 11. Plot 1251 shows an example AIF curve 1252 and an example VOF curve 1254 for a first patient, plotted as HU as a function of time (as explained above with respect to FIG. 12A). Plot 1251 further includes five zones determined according to the method of FIG. 11. Zone transition times are shown by dashed lines. A first transition time is shown at t1, where zone 1 transitions to zone 2; a second transition time is shown at t2, where zone 2 transitions to zone 3; a third transition time is shown at t3, where zone 3 transitions to zone 4; and a fourth transition time is shown at t4, where zone 4 transitions to zone 5.

Plot 1260 shows an example AIF curve 1262 and an example VOF curve 1264 for a second patient, plotted as HU as a function of time (as explained above with respect to FIG. 12A). Plot 125160 further includes five zones determined according to the method of FIG. 11. Zone transition times are shown by dashed lines. A first transition time is shown at t1, where zone 1 transitions to zone 2; a second transition time is shown at t2, where zone 2 transitions to zone 3; a third transition time is shown at t3, where zone 3 transitions to zone 4; and a fourth transition time is shown at t4, where zone 4 transitions to zone 5.

As appreciated by FIG. 12B, the first patient may have a faster ascent time and a faster descent time than the second patient. As a result, the first zone, third zone, and fourth zone for the first patient may be shorter than the first zone, third zone, and fourth zone, respectively, for the second patient. Further, the transition times for the second patient may be delayed relative to the transition times for the first patient.

By determining the transition times for each patient individually, the times when the frame rate of the scan acquisitions is adjusted may be specifically tailored for each patient. In doing so, the increase in frame rate for the second zone, for example, may be triggered just prior to the arterial ascent knee and the frame rate may be further increased for the third zone, just before the arterial peak. In this way, the adjustment of the acquisition frame rate (e.g., of the second and third zones) may be executed when indicated by the patient's individual physiology. In contrast, prior CTP scan prescriptions may scan with a fixed prescription, which may result in over-scanning of some patients (and thus higher than needed radiation exposure) or under-scanning of other patients.

Thus, method 1100 and the corresponding timeline and plots shown in FIGS. 12A and 12B provides for using available contrast enhancement data (e.g., the AIF or TUC signal) from a first contrast injection and the subsequent acquisitions as input to a machine learning model to estimate the AIF and VOF curves and/or time points of interest of the AIF and VOF curves (e.g., the inflection points of the curves). Leveraging the estimates of the AIF and VOF curves and/or the time points of interest, the transition times between five zones spanning the AIF and VOF curves may be defined, and these transition times may be used to generate a personalized CTP scan prescription. The estimation of the AIF and VOF curves and/or the time points of interest may occur relatively quickly (e.g., under 10 ms) and thus the entire personalized, five zone CTP scan prescription may be completed before the venous curve of the first contrast injection even reaches baseline. While a five zone CTP scan prescription is described herein, it is to be understood that the CTP scan prescription may include more or fewer than five zones, and that transition between zones may occur at times other than the examples provided above. The personalized, adaptive CTP scan prescription may include frame rate changes that are triggered at any suitable time or times as a function of the patient's individual, estimated AIF/VOF curves (or AIF/VOF time points), including frame rate changes triggered before the estimated arterial peak.

Method 1100 described above may be applied in various scan protocols, such as when a CTP is performed following a timing bolus or when a CTA or mCTA is performed first followed by the CTP. In examples where the CTP is performed after a CTA, the scan prescription for the CTP may be generated based on contrast enhancement measured upon contrast agent injection for the CTA or mCTA scan. When a CTA is performed before the CTP, additional measurements of the AIF or TUC signal may be obtained between CTA acquisitions, and all of the CTA information (e.g., the AIF or TUC signal and the information from the mCTA itself) may be used as input to better estimate the remainder of the AIF and the VOF (assuming the VOF was not captured) to establish the optimal timing transition (and acquisition end) timings for personalized five zone CTP prescription.

Further, while the AIF signal may include a direct measurement of time point A (the arterial ascent knee, referred as t(A)), the time when t(A) occurs in the monitoring ROI for the CTA scan (for example, the aortic arch) may be different than when t(A) occurs in the head (e.g., at the circle of Willis) where the CTP acquisitions will actually occur. This difference may be accounted for by adjusting the estimated AIF and VOF curves and/or time points of interest or by adjusting the AIF signal that is entered to the model.

When method 1100 is performed, the scan protocol may result in a streamlined workflow that automatically computes the scan prescription for the CTP scan before the start of the second contrast bolus (for the CTP). In some examples, this may include a fully automated workflow where the system automatically computes and updates the CTP scan prescription, and then actuates the contrast injection to start at the target time (e.g., at the estimated VRTB for the first contrast injection, as explained above with respect to FIG. 9) and proceeds to perform the personalized, five zone CTP scan. In other examples, the workflow may be semi-automatic where the system suggests an update of the CTP scan prescription to the user relative to a fallback, fixed CTP protocol and the user has the opportunity to select or reject the updated CTP scan prescription.

Additionally, when the acquisitions are complete and as projection data is sent for image reconstruction/post-processing, the actual AIF/VOF curves may be generated as a first step to the perfusion map computation. In some examples, a post-scan workflow may include displaying to the user a comparison of the AIF/VOF estimates used to generate the CTP scan prescription vs the actual measured AIF and VOF curves. The differences between the estimated and measured AIF/VOF curves may be used to inform the user of the accuracy of the AIF/VOF estimates, inform the user of any errors in the estimates that might have impacted diagnostic image quality, and/or update the machine learning estimation models.

As explained above, a multi-phase angiography contrast scan, referred as an mCTA, may include acquisitions in three phases of contrast agent enhancement/washout, a first phase that is typically performed at the arterial peak, a second phase that is performed at equilibrium or the venous peak, and a third phase that is performed during late venous/venous return to baseline. A typical head mCTA scan protocol may include a determination of when the arterial peak is to occur using the smart prep AIF measurement described above with respect to FIG. 4. A first acquisition is carried out at the estimated arterial peak, where the head and neck are imaged. Then, two additional acquisitions of the head only are carried out at fixed time points relative to the arterial peak, a second acquisition carried out at 8 seconds (or other suitable time) after the arterial peak and a third acquisition carried out at 16 seconds (or other suitable time) after the arterial peak. Patients that are predicted to have a long venous phase, such as older patients (e.g., over 80) or patients with atrial fibrillation, may have mCTA scan protocols that dictate a fourth acquisition be performed at 24 seconds or other suitable time after the arterial peak.

However, these typical mCTA scan protocols may include the second, third, and/or fourth acquisitions being performed at times other than the target times, e.g., due to patient-to-patient variability in contrast enhancement and washout. Further, for patients with short arterial and/or venous phases, a fixed time mCTA scan may result in a scan that is longer than necessary, while for patients with relatively long venous phases (that are not older or have diagnosed atrial fibrillation), the fixed time mCTA scan may result in low quality diagnostic images if the final acquisition is performed before the venous return to baseline. Thus, according to embodiments disclosed herein, a personalized mCTA ("PmCTA") may be performed, where each acquisition of the mCTA is performed relative to the patient physiology (e.g., as determined from estimated AIF/VOF curves) and without prior knowledge (NPK) of the patient's physiology (e.g., the scan may be performed without relying on a timing bolus or some other prior contrast scan information). For example, an AIF signal obtained according to the smart prep estimation method described above with respect to FIG. 4 may be used to trigger the first mCTA acquisition, and from the AIF signal, the full AIF/VOF curves may be estimated (e.g., via a machine learning model as described above with respect to FIG. 9) and the estimated AIF/VOF curves may be used to time the second and third acquisitions, such that the first acquisition may be performed at the estimated arterial peak, the second acquisition may be performed at the estimated venous peak, and the third acquisition may be performed at the estimated venous baseline. In doing so, standardization in mCTA acquisitions may be provided and the inter-operator/inter-patient/inter-radiologist variability that may result in treatment inefficiencies may be reduced.

FIG. 13 shows a flow chart illustrating a method 1300 for carrying out a personalized mCTA scan. Method 1300 is described with respect to the system and components of FIGS. 1-2 but could be carried out with other systems/components without departing from the scope of this disclosure. Method 1300 may be carried out according to instructions stored in non-transitory memory of a computing device (e.g., computing device 216 of FIG. 2). Method 1300 may include identification of estimated times for acquisitions of an mCTA scan without prior knowledge of patient physiology. Thus, method 1300 may be performed in response to user selection of a scanning protocol that includes an mCTA, such as a stand-alone mCTA or an mCTA followed by a CTP. However, in some examples, method 1300 may be carried out with other mCTA scan protocols, such as an mCTA following a CTP.

At 1302, a non-contrast scan is optionally performed, as explained above with respect to FIG. 9. At 1304, a monitoring region of interest (ROI) for contrast monitoring is optionally identified/positioned, similar to the manner that the monitoring ROI was positioned in method 900 described above. At 1306, a first injection of contrast agent into the patient is performed, similar to the first injection of contrast agent described above with respect to FIG. 9. For example, the first injection may be a contrast bolus and the mCTA described herein may be performed in-flight with the contrast level measurement. At 1308, an AIF or TUC signal is measured upon the first injection. The AIF signal or TUC signal may be measured as explained above with respect to FIG. 9. Because the mCTA is performed in-flight with the contrast level determination, the AIF signal may not necessarily include the arterial peak. Rather, the AIF signal may include measurement of a first segment of the AIF curve, e.g., to before the arterial peak, as shown in FIG. 5. Likewise, if used, the TUC signal may include a measurement of a first segment of the TUC until before the tissue uptake peak as shown in FIG. 8. To measure the AIF signal or the TUC signal, a plurality of images of the monitoring ROI or tissue of interest (e.g., brain) may be reconstructed (e.g., by image reconstructor 230) from projection data obtained by the CT system (e.g., from projection data obtained via detector array 108, which detects x-rays generated by x-ray source 104) with a relatively low x-ray dose (e.g., a tube current of 50 mA or less). The signal intensity (e.g., in HU) of the monitoring ROI or segmented tissue relative to a baseline level for each image may be determined and plotted as a function of time to arrive at the AIF signal or TUC signal.

At 1310, the AIF and VOF curves may be estimated based on the AIF or TUC signal. For example, as explained above with respect to FIG. 9, the AIF or TUC signal may be input into a machine learning model (e.g., a regression model, a neural network, or other suitable model), which may output the estimated AIF and VOF curves. In other examples, the machine learning model may output time points of interest, such as the arterial ascent knee (point A in FIG. 3), arterial peak (point B), and arterial decent knee (point C) of the AIF curve, and venous ascent knee (point P), venous peak (point Q), and venous return to baseline (point R) of the VOF curve, etc., based on the AIF or TUC signal. If the estimated AIF and VOF curves are output from the model, the arterial peak (AP), venous peak (VP), and venous return to baseline (VRTB) may be identified on the estimated AIF and VOF curves.

At 1312, the mCTA scan is carried out with acquisitions that are timed based on the AP, VP, and VRTB. Carrying out the mCTA may include performing a first acquisition at the estimated arterial peak, as indicated at 1314, performing a second acquisition at the estimated venous peak, as indicated at 1316, and performing a third acquisition at the VRTB, as indicated at 1318. In some examples, each of the first, second, and third acquisitions may be of the same anatomical area. In other examples, the first acquisition may be of a different anatomical area than the second and third acquisitions. For example, the first acquisition may be of the head and neck while the second and third acquisitions may be of the head only. In some examples, each of the first, second, and third acquisitions may be performed with the same scan parameters (e.g., same tube current, same tube voltage, etc.). In other examples, one or more of the acquisitions may be performed with different scan parameters (e.g., the first acquisition may be performed with a first, higher tube current and the second and third acquisitions may be performed with a second, lower tube current). While three mCTA acquisitions are described herein, more or fewer mCTA acquisitions may be performed, with the timing of any additional mCTA acquisitions determined based on the output of the model (e.g., the time points discussed above). Further, in some examples, the estimated venous peak and estimated VRTB may be adjusted to account for the differences in timing at the monitoring ROI and at the anatomy that is imaged. For example, the monitoring ROI for the mCTA may be the base of the neck while the second and third acquisitions are of the head, and thus the estimated venous peak and estimated VRTB (e.g., estimated for the neck) may be slightly different than the venous peak and VRTB of the head (e.g., the venous peak and VRTB may be slightly delayed relative to the estimated venous peak and estimated VRTB of the neck).

In some examples, as indicated at 1320, the AIF or TUC signal may be measured in between CTA acquisitions of the mCTA scan. For example, the monitoring ROI may be imaged between acquisitions of the mCTA during non-imaging periods of the scan protocol where the CT system may otherwise be inactive. In doing so, the estimation of the AIF/VOF curves and/or time points of interest may be improved by allowing additional AIF signal or TUC signal to be obtained and input to the machine learning model. In some examples where the AIF signal is used as input to estimate the AIF/VOF curves and/or time points of interest on the AIF/VOF curves, the imaging system table (e.g., table 228) may be moved (e.g., by table motor controller 226) after a CTA acquisition in order to image the monitoring ROI, and the table may be moved again to position the target anatomy (e.g., the head) for imaging. Further, the information from the diagnostic acquisitions themselves may be used to further improve the estimation accuracy of the AIF/VOF curves and/or time points of interest.

At 1322, one or more diagnostic images are reconstructed based on data acquired during the mCTA scan. For example, one or more diagnostic images may be reconstructed using known reconstruction techniques, such as filtered back projection or iterative reconstruction. The one or more diagnostic images may be output to a display device (e.g., display device 232) for display to an operator or a physician, to a storage medium (e.g., mass storage 218) for retrieving at a later time, and so on. Method 1300 may then end.

Thus, method 1300 provides for a personalized, patient-physiology specific mCTA that may be performed without a prior timing bolus or without a contrast bolus of a prior scan. Using the contrast signal (e.g., the AIF or TUC signal) that is measured prior to the first acquisition of the mCTA, the acquisitions of the mCTA may be timed to occur at the arterial peak, venous peak, and VRTB of the patient as estimated from the contrast signal, using a machine learning model. The personalized mCTA scan described herein may be applied to create a streamlined/automated workflow that automatically computes/updates the entire PmCTA prescription before the start of the first acquisition of the mCTA. In doing so, user (e.g., scan technologist) cognitive load may be decreased, as the user does not have to determine if a fourth acquisition is needed. In other examples, the workflow may be semi-automatic where the system suggests an update to the CTA prescription (based on the patient physiology as described with respect to FIG. 13) to the user relative to a fallback fixed CTA protocol and the user has the opportunity to select or reject the updated prescription on-the-fly. Further, the estimation of the AIF/VOF curves or points of interest of the AIF/VOF curves may be strengthened by continuing to measure the AIF or TUC signal between CTA acquisitions and entering the updated measurements to the machine learning model and/or the diagnostic information from the acquisitions may be used to improve the timing estimates of the future acquisitions of the PmCTA.

Additionally, when the acquisitions are complete and as projection data is sent for image reconstruction/post-processing, the actual AIF/VOF curves may be generated as a first step to the collateral map computation. In some examples, a post-scan workflow may include displaying to the user a comparison of the AIF/VOF estimates used to generate the mCTA scan prescription versus the actual measured AIF and VOF curves. The differences between the estimated and measured AIF/VOF curves may be used to inform the user of the accuracy of the AIF/VOF estimates, inform the user of any errors in the estimates that might have impacted diagnostic image quality, and/or update the machine learning estimation models.

FIG. 14 shows a first set of plots 1400 depicting mCTA acquisitions for two example patients overlaid on measured AIF and VOF curves for those patients, where the mCTA acquisitions are timed according to a fixed timing mCTA scan protocol. Plot 1401 shows an AIF curve 1402 and a VOF curve 1404 for a first patient (e.g., in HU as a function of time). Three time points of interest are shown in plot 1401. A first time point 1405 corresponds to when a first mCTA acquisition is performed for the first patient. The first acquisition performed at the first time point 1405 may be performed at the arterial peak for the first patient (point B on the AIF curve). A second time point 1407 corresponds to when a second mCTA acquisition is performed for the first patient. The second acquisition performed at the second time point 1407 may be performed at a fixed time after the arterial peak, herein at 8 seconds after the arterial peak. A third time point 1409 corresponds to when a third mCTA acquisition is performed for the first patient. The third acquisition performed at the third time point 1409 may be performed at a fixed time after the arterial peak, herein at 16 seconds after the arterial peak.

Plot 1410 shows an AIF curve 1412 and a VOF curve 1414 for a second patient (e.g., in HU as a function of time). The second patient may be 80 years old or older and/or the second patient may have atrial fibrillation, and thus the second patient may be predicted to have a long venous descent. Thus, four time points of interest are shown in plot 1410. A first time point 1415 corresponds to when a first mCTA acquisition is performed for the second patient. The first acquisition performed at the first time point 1415 may be performed at the arterial peak for the second patient (point B on the AIF curve). A second time point 1417 corresponds to when a second mCTA acquisition is performed for the second patient. The second acquisition performed at the second time point 1417 may be performed at a fixed time after the arterial peak, herein at 8 seconds after the arterial peak. A third time point 1419 corresponds to when a third mCTA acquisition is performed for the second patient. The third acquisition performed at the third time point 1419 may be performed at a fixed time after the arterial peak, herein at 16 seconds after the arterial peak. A fourth time point 1421 corresponds to when a fourth mCTA acquisition is performed for the second patient. The fourth acquisition performed at the fourth time point 1421 may be performed at a fixed time after the arterial peak, herein at 24 seconds after the arterial peak.

The fixed time protocol used to time the mCTA scan acquisitions may result in an adequate mCTA scan for the first patient, as each of the acquisitions may be performed at or near desired phases of the first patient's AIF and VOF curves. However, the fixed time protocol results in an unnecessary acquisition for the second patient (the third acquisition). Further, the fourth acquisition for the second patient is performed before the VOF curve has returned to baseline, which may result in non-diagnostic images being obtained.

FIG. 15 shows a first set of plots 1500 depicting mCTA acquisitions for the two example patients overlaid on measured AIF and VOF curves for those patients, where the mCTA acquisitions are timed according to a personalized mCTA scan protocol described above with respect to FIG. 13. Plot 1501 shows an AIF curve 1502 and a VOF curve 1504 for a first patient (e.g., in HU as a function of time). The first patient may be the same first patient described above, so that the mCTA acquisitions performed according to the personalized mCTA protocol may be compared to the mCTA acquisitions performed according to the fixed time protocol. Three time points of interest are shown in plot 1501. A first time point 1505 corresponds to when a first mCTA acquisition is performed for the first patient. The first acquisition performed at the first time point 1505 may be performed at the arterial peak for the first patient (point B on the AIF curve). A second time point 1507 corresponds to when a second mCTA acquisition is performed for the first patient. The second acquisition performed at the second time point 1507 may be performed at the venous peak for the first patient (point Q). A third time point 1509 corresponds to when a third mCTA acquisition is performed for the first patient. The third acquisition performed at the third time point 1509 may be performed at the venous return to baseline for the patient (point R).

Plot 1510 shows an AIF curve 1512 and a VOF curve 1514 (e.g., in HU as a function of time) for the second patient (the same second patient as described above). A first time point 1515 corresponds to when a first mCTA acquisition is performed for the second patient. The first acquisition performed at the first time point 1515 may be performed at the arterial peak for the second patient (point B on the AIF curve). A second time point 1517 corresponds to when a second mCTA acquisition is performed for the second patient. The second acquisition performed at the second time point 1517 may be performed at the venous peak (point Q). A third time point 1519 corresponds to when a third mCTA acquisition is performed for the second patient. The third acquisition performed at the third time point 1519 may be performed at the venous return to baseline (point R).

As appreciated by comparing plot 1510 to plot 1410, the personalized mCTA described above with respect to FIG. 13 may result in fewer acquisitions for patients who are have long venous descent times, which may reduce radiation exposure for those patients. Further, for patients having long venous descent times, the timing of the final acquisition may be timed to the venous baseline more accurately. For example, the fourth acquisition of plot 1410 is performed before the actual venous return to baseline, while the third acquisition of plot 1510 is performed at the venous return to baseline. Further, the acquisitions shown in plots 1501 and 1510 may be more accurately timed relative to the venous peak and venous return to baseline that the fixed time acquisitions shown in plots 1401 and 1410, which may increase diagnostic image quality in some examples. By timing the acquisitions of the mCTA based on each patient's individual physiology, consistency in imaging across patients may be improved and diagnostic image quality may be increased, at least for some patients. In doing so, relevant treatments for each patient may be administered and false positive identifications of patient conditions may be reduced, without requiring prior knowledge of the patient's physiology.

As explained previously, some scan protocols include two scans, a perfusion scan and an angiography scan. When performing two scans in a single scanning session (e.g., on the same patient, with one scan following the other scan without intentional delays and in some examples without removing the patient from the imaging system), various protocols have been established to carry out the scan as quickly as possible while still obtained desired diagnostic information. However, these protocols rely on multiple contrast boli, which prolongs the overall scan duration and thus may compromise patient outcomes. Thus, as described in more detail below, the TUC signal described above with respect to FIGS. 5-8 may be used as an input to a model (e.g., a machine learning model, such as the regression model or neural network model explained above) to estimate when the angiography acquisitions should be carried out, while simultaneously performing the perfusion acquisitions. The TUC signal may be obtained during a first portion of the perfusion scan, using data from the perfusion acquisitions. The table may be automatically moved (or the operator may be notified to move the table) just prior to the first angiography acquisition, so that the scan range for the first angiography acquisition may be adjusted to include both the head and the neck (e.g., as opposed to the head-only acquisitions for the perfusion scan) and then the table may be moved back to perform additional perfusion acquisitions in between additional angiography acquisitions. Further, the x-ray tube current may be adjusted for the angiography acquisitions automatically. The entire CTA and CTP scan protocol may be carried out with a single injection of contrast agent, and during a single scanning session (e.g., the patient may remain on the table and/or at least partially within the bore of the imaging system for the entirety of the protocol).

FIG. 16 is a flow chart illustrating a method 1600 for performing a single-bolus mCTA-in-CTP. Method 1600 is described with respect to the system and components of FIGS. 1-2 but could be carried out with other systems/components without departing from the scope of this disclosure. Method 1600 may be carried out according to instructions stored in non-transitory memory of a computing device (e.g., computing device 216 of FIG. 2). Method 1600 may include identification of estimated times for acquisitions of an mCTA scan without prior knowledge of patient physiology, with the identification of the estimated times for mCTA acquisition determined during CTP acquisitions. Thus, method 1600 may be performed in response to user selection of a scanning protocol that includes an mCTA-in-CTP. The example mCTA-in-CTP is described below with respect to a head CTP and a head and neck mCTA, but it is to be understood that the single bolus, mCTA-in-CTP protocol described herein may be applied to scans of other anatomical regions. Further, method described herein with respect to FIG. 16 may apply to CTA-in-CTP scan protocols.

At 1602, a non-contrast scan is optionally performed, as explained above with respect to FIG. 9. At 1604, an injection of contrast agent into the patient is performed, similar to the first injection of contrast agent described above with respect to FIG. 9. For example, the injection may be a contrast bolus and the mCTA-in-CTP described herein may be performed in-flight with the contrast level measurement. At 1606, a first portion of CTP acquisitions are performed. The first portion of CTP acquisitions may be performed at the head of the imaging subject, and thus performing the first portion of the CTP acquisitions may include performing the first portion of the CTP acquisitions with a table of the imaging system (e.g., table 228) at first position. Further, the first portion of CTP acquisitions may be performed with a first tube current and a first tube voltage. The first portion of the CTP acquisitions may commence upon the initiation of the injection of the contrast agent, after a predefined prep delay (e.g., of 5-7 seconds).

At 1608, one or more "coarse" images are reconstructed from the data acquired during the first portion of the CTP acquisitions. The coarse images may be reconstructed using a coarse reconstruction process that has a low computational load and thus may be performed rapidly. Because the images reconstructed at 1608 are not diagnostic images but instead are images reconstructed to monitor the tissue uptake of the contrast agent, the coarse reconstruction process may sacrifice diagnostic quality in order to allow the images to be quickly reconstructed. The coarse reconstruction process may include 128×128 slices that are 5 mm thick, and the reconstruction process may take about 1 second per acquisition.

At 1610, the TUC signal is measured from the coarse images. Measuring the TUC signal may include segmenting, in each coarse image, a tissue of interest, such as the brain. The segmentation process may include thresholding the image, performing an erosion process on the thresholded image, identifying the largest object, and then performing a dilation process. However, other segmentation processes may be carried out without departing from the scope of this disclosure. Once the tissue of interest has been segmented, the overall or average signal intensity (e.g., pixel brightness) for the segmented region may be determined and compared to a baseline intensity (e.g., of that tissue/segmented region prior to contrast injection). The signal intensity of each coarse, segmented image may be determined and plotted as a function of time that the image was acquired. It should be understood that the image reconstruction and tissue segmentation process may be performed anytime that a TUC signal is measured, and thus may apply to any of the methods described herein.

At 1612, an AIF curve and a VOF curve are estimated from the TUC signal and an estimated time for the arterial peak (AP), venous peak (VP), and venous return to baseline (VRTB) are estimated from the AIF and VOF curves. The AIF and VOF curves may be estimated from the TUC signal by inputting the TUC signal into a machine learning model, as described above with respect to FIG. 9. The time to AP, time to VP, and time to VRTB may then be determined from the AIF and VOF curves. Alternatively or additionally, the TUC signal may be input into a machine learning model that outputs the time to AP, time to VP, and time to VRTB.

At 1614, the x-ray tube current may be increased and the table may be moved just prior to the estimated AP. At the estimated AP, a first mCTA acquisition may be performed. The CTP acquisitions may be of the head only, but the first acquisition of the mCTA may be of the head and the neck. Thus, the table may be moved before the first mCTA acquisition at the AP. In one example, the first mCTA acquisition may be performed while maintaining a target time between CTP acquisitions of 3 seconds or less. The moving of the table may be initiated at a predetermined time before the estimated AP, where the predetermined time is how long the table takes to move from the CTP position to the mCTA position, which may be 1.2 seconds in one non-limiting example. At the same time, the tube current may be increased from a first tube current for the CTP acquisitions to a second, higher tube current for the first mCTA acquisition. In one non-limiting example, assuming a gantry speed of 0.5 s/rotation, the first tube current may be 300 mA and the second tube current may be 450 mA. Thus, the first mCTA acquisition may be performed at a different position and a different tube current than the CTP acquisitions and may be performed at the estimated arterial peak of the AIF curve.

At 1616, the table is moved back to the CTP position (e.g., for head only acquisitions) and a second portion of CTP acquisitions are performed at the first, lower tube current. At 1618, the tube current is increased prior to the estimated VP and a second mCTA acquisition is performed at the estimated VP. The second mCTA acquisition may be of the head only, and thus the table may be maintained in the CTP position. The tube current may be increased to the second tube current discussed above, and may be increased only for the second mCTA acquisition (e.g., the CTP acquisitions before and after the second mCTA acquisition may be performed at the lower tube current). At 1620, a third portion of CTP acquisitions may be performed at the lower tube current and at 1622, the tube current is increased prior to the estimated VRTB and a third mCTA acquisition is performed at the estimated VRTB. The third mCTA acquisition may be of the head only, and thus the table may be maintained in the CTP position. The tube current may be increased to the second tube current discussed above, and may be increased only for the third mCTA acquisition (e.g., the CTP acquisitions before and after the third mCTA acquisition may be performed at the lower tube current). At 1624, a fourth portion of CTP acquisitions are performed at the lower tube current. However, in some examples, the fourth portion of CTP acquisitions may be performed at an even lower tube current, such as 120 mAs (where mAs indicates mA seconds, and may correspond to a tube current of 120 mA if gantry speed is one rotation per second). The fourth portion of CTP acquisitions may be a fixed number of acquisitions, such as three acquisitions. Upon completion of the fourth portion of the CTP acquisitions, the active acquisition portion of the m-CTA-in-CTP scan protocol may be completed.

In some examples, method 1600 may include updating the estimated AIF and VOF curves using an updated TUC signal obtained from coarse images reconstructed as the CTA/CTP scan progresses, as indicated at 1626. For example, one or more images may be reconstructed from one or more of the CTP acquisitions, and the tissue segmentation and TUC signal measurement described above may be performed on these images to obtain an updated TUC signal that includes TUC data after the first mCTA acquisition. This updated TUC signal may be entered into the machine learning model to provide an updated/refined estimate of the AIF and VOF curves.

Additionally or alternatively, the estimated time of the AP, VP, and VRTB may be confirmed/updated based on aspects of the TUC, as the TUC signal continues to be measured after the first mCTA acquisition. For example, detector may be executed that is configured to flag that the TUC ascent has begun (e.g., shortly after the time point U on FIG. 6). The time point U should happen before the AP (e.g., time point B) and thus the detector may evaluate the timing of U relative to B as a simple check to identify false early estimates of B. In another example, a derivative analysis may be performed directly on the TUC. The first derivative of TUC should peak before the TUC peak itself and occurs very close to t_AP. Also, the second derivative should exhibit a positive peak just a little prior to the peak of the first derivative. These derivative peaks may be used to improve the estimates of B. In a further example, the TUC itself should peak before t_VP. A simple peak detector may be executed to directly detect the TUC peak (e.g., time point V) and use the knowledge of t(V) to improve estimates of the VP and the VRTB. The peak detector may, for each CTP acquisition, look for a peak that has a double confirm (e.g., two successive CTP acquisitions with lower HU). If a double-confirmed peak is found, the found peak is considered as an internal peak candidate (IPC). If the IPC occurs before 14 seconds (e.g., since the contrast injection), the IPC may be discarded and the process may be repeated on the next IPC. IF the IPC does not occur before 14 seconds, the IPC is further analyzed to determine if the slope of the IPC is greater than 3 HU/s. If so, that IPC is considered a spike and is discarded. If not, the time between the ascent knee and the IPC is determined. If this time is less than 4 seconds, the IPC is considered a spike and discarded. If not, it is determined if the median HU before the IPC is greater than the IPC HU minus 2. If so, the IPC is discarded. If not, the segmented tissue (e.g., brain) volume at the IPC is different from a previous tissue volume by greater than a threshold (e.g., 4.25%), the IPC is discarded. If not, if none of these conditions are triggered, the IPC is confirmed as the tissue peak. In a still further example, the filtered version of the TUC signal (e.g., the first and/or second derivatives) may be used as inputs to a machine learning model (e.g., convolutional neural network) to further improve the estimates of the AIF/VOF curves.

At 1628, one or more diagnostic images are reconstructed based on data acquired during the scan. For example, one or more diagnostic images may be reconstructed using known reconstruction techniques, such as filtered back projection or iterative reconstruction. Images may be constructed for each scan type, e.g., CTA images and CTP images. The one or more diagnostic images may be output to a display device (e.g., display device 232) for display to an operator or a physician, to a storage medium (e.g., mass storage 218) for retrieving at a later time, and so on. Method 1600 may then end.

Thus, method 1600 provides for a single bolus mCTA performed with a CTP that is personalized to the patient without prior knowledge of patient hemodynamics/physiology. The timing of the mCTA acquisitions may be timed to occur between CTP acquisitions. The CTA acquisitions may only differ from the CTP acquisitions in that the tube current for the CTA acquisitions may be higher than the CTP acquisitions and for the first CTA acquisition, the acquisition may be of the head and neck rather than the head only, and thus scan range for the first CTA acquisition may be inferior to the CTP scan range. The head portion of the CTA may be used for the CTA as well as for the CTP. In other words, the second and third CTA acquisitions may be used to reconstruct the CTP images as well as the CTA images. To enable a single contrast injection mCTA-in-CTP that is personalized to the patient, the patient physiology with respect to the contrast agent uptake/washout is determined using the TUC signal. The TUC signal may be measured using only images of the head, and does not require an ROI placement on an artery or vein. Thus, the TUC signal may be measured during the first portion of the CTP acquisitions. The timing of the mCTA acquisitions may be based on the patient physiology determined from the TUC signal, e.g., the first acquisition may be performed at an estimated arterial peak, the second acquisition may be performed at an estimated venous peak, and a third acquisition may be performed at an estimated venous return to baseline.

Further, the CTP acquisitions may be performed according to a personalized CTP protocol. For example, the duration of the scan protocol may be divided up into zones defined by certain contrast events, such as the AP, VP, VRTB, etc. Each zone may have specified scan parameters for the CTP acquisitions, such as a specified frame rate, tube current, etc., that may be different between zones. A personalized, four-zone CTP is described below with respect to FIG. 18, and this protocol may be applied to the CTP performed in method 1600.

FIG. 17 shows an example plot 1700 depicting CTP and mCTA acquisitions for a patient overlaid on estimated AIF and VOF curves for that patients, where the mCTA acquisitions are timed according to the mCTA-in-CTP scan protocol of method 1600. Plot 1700 shows an estimated AIF curve 1702 and an estimated VOF curve 1704 for the patient (e.g., in HU as a function of time), estimated from the TUC signal using a machine learning model as described above. Plot 1700 also shows scanning events/acquisitions (with the tube current for each acquisition of the CT imaging system) carried out according to the mCTA-in-CTP scan protocol. Each solid line shows one CTP acquisition and each dashed line shows one CTA acquisition. Thus, a first portion of CTP acquisitions occurs before the first CTA acquisition (at the estimated AP of the AIF curve 1702), a second portion of CTP acquisitions occurs after the first CTA acquisition and before a second CTA acquisition (at the estimated VP of the VOF curve 1704), a third portion of CTP acquisitions occurs after the second CTA acquisition and before a third CTA acquisition (at the estimated VRTB), and a fourth portion of CTP acquisitions occurs after the third CTA acquisition.

Additionally, plot 1700 shows that the CTP acquisitions may be performed at different frame rates in different zones of the CTP/CTA protocol. For example, the CTP acquisitions from the prep delay (of 7 seconds) until the VP may be performed at a first frame rate (e.g., one/1.8 s), the CTP acquisitions from the VP until the VRTB may be performed at a second frame rate (e.g., one/3.25 s), and the CTP acquisitions thereafter may be performed at a third frame rate (e.g., one/5 s).

While the angiography and perfusion acquisitions are shown in FIG. 17 as being performed at the same x-ray tube current, it is be understood that the angiography acquisitions may be performed at the same or different x-ray tube current and/or voltage as the perfusion acquisitions. For example, the angiography acquisitions may be performed at a higher tube current than the perfusion acquisitions. Additionally or alternatively, the angiography acquisitions may be performed at a higher tube voltage than the perfusion acquisitions (e.g., the angiography acquisitions may be performed at 120 kV and the perfusion acquisitions may be performed at 80 kV).

As explained above, a personalized, five zone CTP scan protocol may enable a CTP scan to be performed in a manner that generates high quality diagnostic images without exposing a patient to undue radiation or prolonging the scan duration. However, the five-zone CTP scan described above with respect to FIG. 11 relies on a timing bolus or other prior contrast injection in order to set the five-zone scan prescription. CTP scans, when used during acute stroke care, may be used by clinicians as a tool to decide if a particular patient will benefit from endovascular thrombectomy. Due to the time sensitive nature of acute stroke care and the scan and reconstruction duration of a CTP scan, the CTP scan may be performed as soon as a patient arrives at a medical facility, before patient information and any recent patient hemodynamic information is available. Thus, under certain clinical situations, it may not be practical to perform the timing bolus to obtain the patient hemodynamic/contrast agent response information.

Thus, as will be described in more detail below, a personalized four zone CTP scan may be performed when no prior knowledge of the patient's contrast agent response is available. The four-zone CTP collapses the first two zones of the five-zone CTP into a single zone, and adjusts aspects of the scan parameters at each zone transition in a manner similar to the five-zone CTP.

FIG. 18 shows a flow chart illustrating a method 1800 for carrying out a personalized four-zone CTP scan. Method 1800 is described with respect to the system and components described above with respect to FIGS. 1-2 but could be carried out with other systems/components without departing from the scope of this disclosure. Method 1800 may be carried out according to instructions stored in non-transitory memory of a computing device (e.g., computing device 216 of FIG. 2). Method 1800 may include identification of estimated times of the transitions between four zones of a CTP scan, which may be used to determine a scan prescription for carrying out the CTP scan. Thus, method 1800 may be performed in response to user selection of a scanning protocol that includes a CTP, such as a stand-alone CTP, a CTA followed by a CTP, a CTP followed by a CTA, a combined CTP and CTA, etc.

At 1802, a non-contrast scan is optionally performed, as explained above with respect to FIG. 9. At 1804, an injection of contrast agent into the patient is performed, similar to the first injection of contrast agent described above with respect to FIG. 9 (e.g., the injection may be a contrast bolus for an in-flight CTP scan and may be the only contrast injection performed for the CTP scan). At 1806, scanning in the first zone of the CTP protocol is initiated with default scan parameters. The default scan parameters may include a medium temporal resolution that is slower than the frame rate of the subsequent zone but faster than the frame rate of the final zone. In one example, the default scan parameters may include a frame rate of one acquisition each 2-4 seconds.

At 1808, a TUC signal is measured from images reconstructed with projection data acquired during the scanning in the first zone of the CTP protocol. The TUC signal may be measured as explained above with respect to FIG. 16, and thus may include measurement of a first segment of the TUC (e.g., until before the tissue uptake peak as shown in FIG. 8 or until just after the tissue uptake peak as shown in FIG. 7). To measure the TUC signal, a plurality of images of the imaging area (e.g., head) may be reconstructed (e.g., by image reconstructor 230) from projection data obtained by the CT system (e.g., from projection data obtained via detector array 108, which detects x-rays generated by x-ray source 104) using the coarse reconstruction process, and the tissue of interest (e.g., the brain) may be segmented in the images. The signal intensity (e.g., in HU) of the tissue of interest relative to a baseline level for each image may be determined and plotted as a function of time to arrive at the TUC signal.

At 1810, the AIF and VOF curves may be estimated based on the TUC signal. For example, as explained above with respect to FIG. 9, the TUC signal may be input into a machine learning model (e.g., a regression model, a neural network, or other suitable model), which may output the estimated AIF and VOF curves. In other examples, the machine learning model may output time points of interest, such as the arterial ascent knee (point A in FIG. 3), arterial peak (point B), and arterial decent knee (point C) of the AIF curve, and venous ascent knee (point P), venous peak (point Q), and venous return to baseline (point R) of the VOF curve, etc., based on the TUC signal. The four zones of the CTP scan may then be identified base on the estimated AIF and VOF curves and/or the estimated time points of interest.

As one example, the first zone may begin when the injection of contrast agent begins or the first zone may begin after a predefined delay after the injection has commenced. A first transition from the first zone to the second zone may be identified based on the timing of arterial peak (point B), for example, the first transition may be estimated to occur two seconds before the arterial peak. A second transition from the second zone to the third zone may be identified based on the venous peak (point Q), for example, the second transition may be estimated to occur two seconds after the venous peak. A third transition from the third zone to the fourth zone may be identified based on the venous return to baseline (VRTB, point R), for example, the third transition may be estimated to occur two seconds after the VRTB. The fourth zone may end at a fixed time after the VRTB, such as fourteen seconds after VRTB. Although four zones are described herein, the personalized CTP scan may include more or fewer than four zones without departing from the scope of this disclosure. For example, the first and second zones may be combined into a single zone, resulting in three zones, where the first zone has a relatively fast frame rate (e.g., one acquisition every 2 seconds). In another example, an additional zone may be appended after 14 seconds past VRTB (e.g., after the fourth zone), with the additional zone extending until 90 seconds post-VRTB and having a slower frame rate of one acquisition every 10 seconds.

At 1812, one or more scan parameters are adjusted as the CTP scan progresses, based on the identified zones/zone transitions. For example, as explained above, values for one or more scan parameters may be adjusted for one or more zones, such as frame rate, tube current, tube voltage, etc. Adjusting the scan parameters may include increasing the frame rate from the default frame rate when entering the second zone, as indicated at 1814. For example, the frame rate may be increased to one acquisition every 1.8 seconds during the second zone. Adjusting the scan parameters may include decreasing the frame rate when entering the third zone, as indicated at 1816. For example, the frame rate may be reduced to one acquisition every 3.25 seconds during the third zone. Adjusting the scan parameters may include decreasing the frame rate when entering the fourth zone, as indicated at 1818. For example, the frame rate may be reduced to one acquisition every 5 seconds during the fourth zone.

In some examples, a CTA may be performed along with the CTP, referred to as a CTA-in-CTP scan. In such examples, mCTA acquisitions may be selected from CTP phases based on the estimated AIF and VOF curves, as indicated at 1820. For example, the CTA acquisitions may be selected to occur at the arterial peak, venous peak, and VRTB. The CTA may be a "virtual" CTA where select CTP acquisitions may be used to reconstruct CTA images, and these select CTP acquisitions may be chosen based on the estimated AIF and VOF curves. For example, the estimated AIF, TUC, and/or VOF curves may be displayed with selectable points. A user may select the selectable points corresponding to the CTP acquisitions that are to be used for the CTA (e.g., acquisitions 4, 7, and 11) and instruct the system to generate TrueFidelity reconstructions of those acquisitions to generate a virtual head-only CTA from the CTP. In other examples, the CTA may be a multi-phase CTA (referred to as an mCTA) where a first head and neck acquisition is followed by two head-only acquisitions. The timing of these mCTA acquisitions may be selected based on the estimated AIF/VOF curves as described above, and the acquisitions may be performed at a different tube current than the CTP acquisitions, at least in some examples. When performing the mCTA in the CTP, the table may be moved in order to perform the first mCTA acquisition and then moved back to continue the CTP acquisitions, as described above with respect to FIG. 16.

Thus, the four-zone CTP scan may start at the first zone and may include scanning in the first zone at a first frame rate, first tube current, etc.; transitioning to the second zone at the first transition time (which may be based on the estimated AP as explained above) and scanning in the second zone at a second frame rate, second tube current, etc.; transitioning to the third zone at the second transition time (which may be based on the estimated VP as explained above) and scanning in the third zone at a third frame rate, third tube current, etc.; and transitioning to the fourth zone at the third transition time (which may be based on the VRTB as explained above) and scanning in the fourth zone at a fourth frame rate, fourth tube current, etc. The scanning in the fourth zone may stop after a suitable number of acquisitions have been performed, such as three. In some examples, the first frame rate may be different than the second frame rate, the second frame rate may be different than the third frame rate, and the third frame rate may be different than the fourth frame rate. In some examples, one or more of the zones may have the same frame rate. In some examples, one or more of the zones may have the same tube current and/or one or more of the zones may have different tube current. In some examples, carrying out the CTP scan may include performing the mCTA acquisitions at the selected/indicated times.

In some examples, method 1800 may include updating the estimated AIF and VOF curves using an updated TUC signal obtained from coarse images reconstructed as the CTP scan progresses, as indicated at 1822. For example, one or more images may be reconstructed from one or more of the CTP acquisitions, and the tissue segmentation and TUC signal measurement described above may be performed on these images to obtain an updated TUC signal that includes TUC data after the first zone of CTP acquisitions. This updated TUC signal may be entered into the machine learning model to provide an updated/refined estimate of the AIF and VOF curves, as explained above with respect to FIG. 16.

At 1824, one or more diagnostic images are reconstructed based on data acquired during the CTP scan. For example, one or more diagnostic images may be reconstructed using known reconstruction techniques, such as filtered back projection or iterative reconstruction. When a CTA is carried out with the CTP, images may be constructed for each scan, e.g., CTA images and CTP images. The one or more diagnostic images may be output to a display device (e.g., display device 232) for display to an operator or a physician, to a storage medium (e.g., mass storage 218) for retrieving at a later time, and so on. Method 1800 may then end.

FIG. 19 shows an example timeline of a four zone, personalized CTP scan carried out according to the method of FIG. 18. Timeline 1900 includes a first plot 1901 showing estimated contrast levels determined from a TUC estimation method. As such, plot 1201 includes an estimated AIF curve 1902, an estimated VOF curve 1904, and an estimated TUC 1906, as explained above with respect to FIGS. 3-8. Plot 1910 shows scanning events (with the tube current for each acquisition period of the CT imaging system). Each plot is a function of time and the plots are time aligned. Dashed lines show time points of interest, herein the identified zone transitions.

The first zone (zone 1) may commence at time t0, which may correspond to the beginning of a contrast agent injection. After a prep delay (e.g., of 5 seconds), scanning may commence. In zone 1, the acquisitions may occur at a first frame rate. The first frame rate may be one acquisition every 2.8 seconds. The first transition may be estimated to occur at time t1, which may be two seconds before point B on the AIF curve 1902. When transitioning to the second zone (zone 2) at time t1, the acquisition frame rate may be increased, such that scanning occurs at a second frame rate in zone 2. The second frame rate may be one acquisition every 2.1 seconds. The second transition may be estimated to occur at time t2, which may be two seconds after point Q on the VOF curve 1904. When transitioning to the third zone (zone 3) at time t2, the acquisition frame rate may be decreased, such that scanning occurs at a third frame rate in zone 3. The third frame rate may be one acquisition every 3.5 seconds. The third transition may be estimated to occur at time t3, which may be two seconds after point R on the VOF curve 1904. When transitioning to the fourth zone (zone 4) at time t3, the acquisition frame rate may be decreased, such that scanning occurs at a fourth frame rate in zone 4. The fourth frame rate may be one acquisition every 4.9 seconds. In some examples, only three acquisitions may occur in zone 4, and then the CTP scan may end. In some examples, the tube current and voltage may remain contrast for each zone. In other examples, the tube current may be adjusted in one or more zones. For example, the tube current may be lowered by 10-25% for zones 3 and 4, or just zone 4, or for zones 1, 3, and 4.

The four zone CTP described herein may include exactly four zones. In other examples, the four zone CTP described herein may be modified to include more or fewer zones, such as three zones or five zones. Further, rather than have a discrete number of defined zones, the personalized CTP protocol described herein may use the contrast signal measured during a first portion of the CTP scan to time and/or set parameters for subsequent acquisitions of the CTP scan (and any CTA acquisitions, when performed). The four zone CTP scan protocol may be differentiated from the five zone CTP scan protocol discussed above with respect to FIG. 11 in that the four zone CTP scan protocol may rely on a contrast signal measured in-flight (e.g., using the same contrast bolus, and thus no or little prior patient knowledge) while the five zone CTP protocol may rely on a contrast signal measured with a separate contrast bolus and thus the prescription is set with knowledge of patient hemodynamics. Further, while the zone transitions described above are based on points of interest of the AIF and VOF curves, the zone transitions may additionally or alternatively be based on the TUC. For example, the first transition at time t1 may be based on time point U (e.g., a certain about of time following U, such as three seconds), the second transition at time t2 may be based on time point V (e.g., two seconds after V), and the third transition time at time t3 may be based on time point W (e.g., two seconds after W).

Thus, the systems and methods disclosed herein provide for estimating when various contrast agent time points/curves will occur for a specific patient, using (at least initially) a short measured segment (referred to as a contrast signal) of a contrast enhancement curve measured at a monitoring area as an input to a machine learning model to predict the remaining contrast agent time points or curves. The contrast enhancement curve may be an arterial inflow function (AIF) curve, and the segment of the AIF curve may be measured at an artery of the patient, in an example. In another example, the contrast enhancement curve may be a venous outflow function (VOF) curve, and the segment of the VOF curve may be measured at a vein of the patient. In a still further example, the contrast enhancement curve may be a tissue uptake curve (TUC), and the segment may be measured at a tissue of interest (e.g., the brain), where the tissue is segmented in a plurality of images. In some examples, more than one contrast enhancement curve may be measured (e.g., both the AIF and the VOF may be measured). Based on these estimated time points, various contrast scan actions may be carried out. As explained above with respect to FIG. 9, the optimal timing to deliver a second contrast bolus following delivery of a first contrast bolus may be determined based on an estimated venous return to baseline of the first contrast bolus, using a measured segment of a contrast enhancement curve of the first contrast bolus. In another example, additionally or alternatively, the predicted time points may be used to generate a five-zone CTP scan prescription for carrying out an adaptive, personalized CTP scan, as explained above with respect to FIG. 11. The five-zone CTP scan prescription may be carried out with a second contrast injection following a first contrast injection, and the time points may be estimated using a measured segment of a contrast enhancement curve of the first contrast injection. In another example, additionally or alternatively, the time points estimated herein may be used to generate a four-zone CTP scan prescription for carrying out an adaptive, personalized CTP scan, as explained above with respect to FIG. 18. The four-zone CTP scan prescription may be carried out with a single contrast injection, and the time points may be estimated using a measured segment of a contrast enhancement curve of the single contrast injection. In another example, additionally or alternatively, the time points estimated herein may be used to time acquisitions of an mCTA scan where no prior knowledge of patient hemodynamics is available, whether as a stand-alone mCTA (as described above with respect to FIG. 13) or as part of an mCTA-in-CTP (as described above with respect to FIG. 16). For the mCTA scans, the time points may be estimated using a measured segment of a contrast enhancement curve of a single contrast injection, and the mCTA scan may be carried out with enhancement provided from that single contrast injection.

The time points may be estimated from an AIF signal or a TUC signal. As explained above with respect to FIGS. 3-5, the AIF signal may be a segment of an AIF curve measured at an arterial ROI. As explained above with respect to FIGS. 6-8, the TUC signal may be a segment of a TUC measured at a segmented tissue region. The TUC signal may be robust to patient movement, given that the "ROI" is the segmented tissue and thus the ROI moves along with the patient from image to image. Further, the TUC signal may be measured at the head, rather than the neck, which may eliminate the need to adjust the imaging region of interest to go between the measurement of the TUC signal and diagnostic acquisitions.

A first estimation method, which may encompass the aTB method or the first TUC method, uses as input a curve segment of either the AIF or the TUC that ends at one or more acquisitions after the respective peak (e.g., arterial or tissue). A second estimation method, which may encompass the aSP or the second TUC method, uses as its input a curve segment of either the AIF or the TUC that ends at one or more passes before the respective peak (e.g., arterial or tissue). Each estimation method includes a model. In the training for the models, if the AIF segment is the input, the measured signal for training the model is the AIF curve segment and/or features from the AIF curve segment. The ground truth for training the model may be the collection of times for A, B, C, P, Q, and R on the AIF and VOF curves and possibly HU values as well. If the TUC segment is the input, the measured signal for training the model is the TUC curve segment and/or features from the TUC curve segment. The ground truth for training may be same as above (e.g., A, B, C, P, Q, and R times and possibly HU values as well).

In any of the methods described herein, once the time points have been estimated and the scan protocols commence based on the estimated time points, the AIF or TUC signal may continue to be measured in order to determine an actual AIF curve, VOF curve, and/or TUC. If an acquisition timed based on an estimated time point (e.g., an mCTA acquisition) is determined to have been acquired at an incorrect time, an operator may be notified so that the acquisition may be repeated at the correct time. This may include performing an additional scan, with an additional contrast agent bolus, but may reduce undue reconstruction time, as the operator may be notified before full diagnostic reconstruction has begun, rather than waiting until the diagnostic images have been reconstructed to determine that one or more scans did not produce sufficient diagnostic images. Further, in any of the methods described herein, when the acquisitions are complete and as projection data is sent for image reconstruction/post-processing, the actual AIF/VOF/TUC curves may be generated and displayed to the user as comparison of the AIF/VOF/TUC estimates used to generate the scan prescription(s) described herein versus the actual measured AIF, VOF, and/or TUC curves. The differences between the estimated and measured AIF/VOF/TUC curves may be used to inform the user of the accuracy of the AIF/VOF/TUC estimates, inform the user of any errors in the estimates that might have impacted diagnostic image quality, and/or update the machine learning estimation models.

A technical effect of the disclosure is that a second contrast injection following a first contrast injection may be timed on a patient by patient basis, which may reduce the time for diagnostic imaging while maintaining the diagnostic quality of the images. Another technical effect of the disclosure is that an adaptive, personalized multiple zone perfusion scan may be performed, which may increase diagnostic image quality and/or reduce patient radiation exposure. Another technical effect of the disclosure is that angiography scan acquisitions may be timed based on patient hemodynamics/physiology, which may increase diagnostic image quality and/or reduce patient radiation exposure. A further technical effect of the disclosure is that scan durations may be reduced and subsequent patient treatment decisions may be more accurate, reducing unnecessary transfers to other medical facilities and improving patient outcomes.

An embodiment for a method is provided, the method including, upon a first contrast injection, processing acquired projection data of a subject to measure a contrast signal of the first contrast injection; estimating a time when a venous return to baseline (VRTB) of the first contrast injection is to occur based on the contrast signal; and commanding initiation of a second contrast injection at the estimated time. In a first example of the method, the acquired projection data is of an arterial region of interest (ROI) and the contrast signal comprises a segment of an arterial inflow function (AIF) curve. In a second example of the method, which optionally includes the first example, the segment starts at a first time corresponding to commencement of the first contrast injection and ends at a second time corresponding to a point of the AIF curve prior to a peak of the AIF curve. In a third example of the method, which optionally includes one or both of the first and second examples, the segment starts at a first time corresponding to commencement of the first contrast injection and ends at a second time corresponding to a point of the AIF curve after a peak of the AIF curve. In a fourth example of the method, which optionally includes one or more or each of the first through third examples, the acquired projection data is processed to segment tissue of interest of the subject in a plurality of reconstructed images and the contrast signal comprises a segment of a tissue uptake curve measured from the segmented tissue. In a fifth example of the method, which optionally includes one or more or each of the first through fourth examples, the segment starts at a first time corresponding to commencement of the first contrast injection and ends at a second time corresponding to a point of the tissue uptake curve prior to a peak of the tissue uptake. In a sixth example of the method, which optionally includes one or more or each of the first through fifth examples, the segment starts at a first time corresponding to commencement of the first contrast injection and ends at a second time corresponding to a point of the tissue uptake curve after a peak of the tissue uptake curve. In a seventh example of the method, which optionally includes one or more or each of the first through sixth examples, estimating the time when the VRTB is to occur includes entering the contrast signal as input to a machine learning model trained to output the estimated time when the VRTB is occur as a function of the contrast signal. In an eighth example of the method, which optionally includes one or more or each of the first through seventh examples, the first contrast injection is a timing bolus, and further comprising initiating a contrast scan of the subject upon initiation of the second contrast injection. In a ninth example of the method, which optionally includes one or more or each of the first through eighth examples, the method further includes, after acquiring the projection data to measure the contrast signal, initiating a first contrast scan of the subject, and upon initiation of the second contrast injection, initiating a second contrast scan of the subject.

Another embodiment for a method is provided, the method including, upon a first injection of a contrast agent to a subject, measuring a contrast level of the contrast agent of the subject until the contrast level reaches a first point on a contrast level curve to generate a contrast signal; initiating a first contrast scan of the subject with the imaging system; determining when an estimated venous return to baseline of the contrast agent is going to occur based on the contrast signal; commanding a second injection of the contrast agent to the subject be performed at the estimated venous return to baseline; and initiating a second contrast scan of the subject. In a first example of the method, the imaging system is a computed tomography (CT) system, the first contrast scan is a CT angiography scan, and the second contrast scan is a CT perfusion scan. In a second example of the method, which optionally includes the first example, determining when the estimated venous return to baseline of the contrast agent is going to occur based on the contrast signal comprises determining when the estimated venous return to baseline of the contrast agent is going to occur via a machine learning model using the contrast signal as input to the machine learning model. In a third example of the method, which optionally includes one or both of the first and second examples, the first contrast scan is initiated in response to determining that the contrast level has reached the first point on the contrast level curve. In a fourth example of the method, which optionally includes one or more or each of the first through third examples, the contrast level curve is an arterial inflow function curve and wherein the first point on the arterial inflow function curve is before a peak of the arterial inflow function curve.

An embodiment for a system is provided, including an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: upon a first contrast injection, process projection data of a subject received from the DAS to measure a contrast signal of the first contrast injection; estimate a time when a predetermined event of the first contrast injection is to occur based on the contrast signal; and command a second contrast injection be initiated at the estimated time. In a first example of the system, the predetermined event of the first contrast injection comprises a venous return to baseline of the first contrast injection or a first harmonic of an arterial inflow function curve of the first contrast injection. In a second example of the system, which optionally includes the first example, the system further includes a display device operably coupled to the computer, and commanding the second contrast injection be initiated at the estimated time includes displaying a notification on the display device commanding the second contrast injection be initiated. In a third example of the system, which optionally includes one or both of the first and second examples, the non-transitory memory stores a machine learning model configured to estimate the time when the VRTB is to occur based on the contrast signal. In a fourth example of the system, which optionally includes one or more or each of the first through third examples, the machine learning model is a regression model or a neural network.

An embodiment for a method is provided, the method including, upon an injection of a contrast agent, processing acquired projection data of a monitoring area of a subject to measure a contrast signal of the contrast agent; estimating two or more target times of the contrast agent at the monitoring area of the subject based on the contrast signal; and carrying out a contrast scan that includes a two or more acquisitions each performed at a respective target time. In a first example of the method, estimating the two or more target times of the subject based on the contrast signal comprises estimating an arterial peak time, a venous peak time, and a venous return to baseline time of the contrast agent at the monitoring area of the subject based on the contrast signal, and wherein carrying out the contrast scan includes performing an acquisition at the arterial peak time, an acquisition at the venous peak time, and an acquisition at the venous return to baseline time. In a second example of the method, which optionally includes the first example, estimating the two or more target times of the subject based on the contrast signal comprises entering the contrast signal as input to a machine learning model trained to output the two or more target times as a function of the contrast signal. In a third example of the method, which optionally includes one or both of the first and second examples, the method further includes updating the contrast signal with processed projection data of the monitoring area acquired between acquisitions of the two or more acquisitions, and entering the updated contrast signal as input to the machine learning model to update the estimation of the two or more target times. In a fourth example of the method, which optionally includes one or more or each of the first through third examples, the monitoring area is an artery and the contrast signal comprises a segment of an arterial inflow function (AIF) curve, and wherein the segment starts at a first time corresponding to commencement of the first contrast injection and ends at a second time corresponding to a point of the AIF curve prior to a peak of the AIF curve. In a fifth example of the method, which optionally includes one or more or each of the first through fourth examples, the monitoring area is a vein and the contrast signal comprises a segment of a venous outflow function (VOF) curve. In a sixth example of the method, which optionally includes one or more or each of the first through fifth examples, the monitoring area is a brain of the subject and the contrast signal comprises a segment of a tissue uptake curve. In a seventh example of the method, which optionally includes one or more or each of the first through sixth examples, the segment starts at a first time corresponding to commencement of the first contrast injection and ends at a second time corresponding to a point of the tissue uptake curve prior to a peak of the tissue uptake.

Another embodiment for a method for an imaging system is provided, the method including performing an injection of a contrast agent to a subject; measuring a contrast level of a monitoring region of interest (ROI) of the subject with the imaging system until the contrast level reaches a first point on a contrast level curve to generate a contrast signal; determining when each of an estimated arterial peak, an estimated venous peak, and an estimated venous return to baseline of the contrast agent is going to occur based on the contrast signal; and performing a respective contrast scan acquisition of the subject with the imaging system at each of the estimated arterial peak, the estimated venous peak, and the estimated venous return to baseline. In a first example of the method, the imaging system is a computed tomography (CT) system and each contrast scan acquisition is a CT angiography scan acquisition. In a second example of the method, which optionally includes the first example, determining when each of the estimated arterial peak, the estimated venous peak, and the estimated venous return to baseline of the contrast agent is going to occur based on the contrast signal comprises determining when each of the estimated arterial peak, the estimated venous peak, and the estimated venous return to baseline of the contrast agent is going to occur via a machine learning model using the contrast signal as input to the machine learning model. In a third example of the method, which optionally includes one or both of the first and second examples, the contrast level curve is an arterial inflow function curve, the arterial peak is a peak of the arterial inflow function curve, and wherein the first point on the arterial inflow function curve is before the arterial peak. In a fourth example of the method, which optionally includes one or more or each of the first through third examples, each respective contrast scan acquisition is performed after the injection of the contrast agent and without any additional intervening injections of the contrast agent.

An embodiment for a system is provided, including an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: upon an injection of a contrast agent, process projection data of a monitoring region of interest (ROI) of a subject from the DAS to measure a contrast signal of the contrast agent; estimate a two or more target times of the subject based on the contrast signal; and perform a contrast scan that includes two or more acquisitions each performed at a respective target time. In a first example of the system, a first target time of the two or more target times corresponds to an arterial peak of the contrast agent at the monitoring ROI of the subject, a second target time of the two or more target times corresponds to a venous peak of the contrast agent at the monitoring ROI of the subject, and a third target time of the two or more target times corresponds to a venous return to baseline of the contrast agent at the monitoring ROI of the subject. In a second example of the system, which optionally includes the first example, the contrast scan in a multi-phase angiography scan, and wherein the first acquisition is of a head and neck of the subject and each of the second and third acquisitions are only of the head of the subject. In a third example of the system, which optionally includes one or both of the first and second examples, the multi-phase angiography scan is performed after the injection of the contrast agent and without any additional intervening injections of the contrast agent. In a fourth example of the system, which optionally includes one or more or each of the first through third examples, the non-transitory memory stores a machine learning model configured to estimate each of the two or more target times based on the contrast signal. In a fifth example of the system, which optionally includes one or more or each of the first through fourth examples, the machine learning model is a regression model. In a sixth example of the system, which optionally includes one or more or each of the first through fifth examples, the machine learning model is a neural network.

An embodiment for a method is provided, the method including, upon a first injection of a contrast agent, processing acquired projection data of a monitoring area of a subject to measure a contrast signal of the contrast agent; determining when each of a plurality of zones of a contrast scan are estimated to occur based on the contrast signal; generating a scan prescription for the contrast scan based on when each of the plurality of zones are estimated to occur; and upon a second injection of contrast agent, performing the contrast scan according to the scan prescription. In a first example of the method, determining when each of the plurality of zones of the scan protocol are estimated to occur based on the contrast signal comprises determining a plurality of estimated transition times between zones, including an estimated first transition time when a first zone is estimated to transition to a second zone, an estimated second transition time when the second zone is estimated to transition to a third zone, an estimated third transition time when the third zone is estimated to transition to a fourth zone, and an estimated fourth transition time when the fourth zone is estimated to transition to a fifth zone. In a second example of the method, which optionally includes the first example, the plurality of estimated transition times are estimated from an arterial inflow function (AIF) curve and a venous outflow function (VOF) curve output from a machine learning model, where the contrast signal is entered as input to the machine learning model. In a third example of the method, which optionally includes one or both of the first and second examples, generating the scan prescription includes setting one or more scan parameters for each zone. In a fourth example of the method, which optionally includes one or more or each of the first through third examples, at least two zones of the plurality of zones differ in one or more of a frame rate and a tube current. In a fifth example of the method, which optionally includes one or more or each of the first through fourth examples, performing the contrast scan comprises commanding initiation of a second injection of the contrast agent and then performing one or more acquisitions of the contrast scan according to the scan prescription. In a sixth example of the method, which optionally includes one or more or each of the first through fifth examples, commanding initiation of the second injection includes commanding initiation of the second injection at a target time relative to the first injection, the target time determined based on the contrast signal. In a seventh example of the method, which optionally includes one or more or each of the first through sixth examples, the monitoring area is an artery and the contrast signal comprises a segment of an arterial inflow function (AIF) curve, and wherein the segment starts at a first time corresponding to commencement of the first contrast injection and ends at a second time corresponding to a point of the AIF curve prior to a peak of the AIF curve. In an eighth example of the method, which optionally includes one or more or each of the first through seventh examples, the monitoring area comprises brain parenchyma of the subject and the contrast signal comprises a segment of a tissue uptake curve, and wherein the segment starts at a first time corresponding to commencement of the first contrast injection and ends at a second time corresponding to a point of the tissue uptake curve prior to a peak of the tissue uptake.

Another embodiment for a method is provided, the method including, upon a first injection of a contrast agent, processing acquired projection data of a monitoring area of a subject to measure a contrast signal of the contrast agent; determining when each of a plurality of transition times between respective zones of a plurality of zones of a contrast scan are estimated to occur based on the contrast signal; generating a scan prescription for the contrast scan based on when each of the plurality of transition times are estimated to occur, including for at least a first transition time of the plurality of transition times, adjusting a frame rate of the imaging system from a first frame rate to a second frame rate at the first transition time; commanding initiation of a second injection of the contrast agent at a time determined based on the contrast signal; and upon initiation of the second injection, performing the contrast scan with the imaging system according to the scan prescription. In a first example of the method, the plurality of zones includes five zones and the plurality of transition times includes the first transition time and three additional transition times. In a second example of the method, which optionally includes the first example, a first zone of the five zones commences upon initiation of the second injection and ends at the first transition time, a second zone of the five zones commences at the first transition time and ends at a second transition time, a third zone of the five zones commences at the second transition time and ends at a third transition time, a fourth zone of the five zones commences at the third transition time and ends at a fourth transition time, and a fifth zone of the five zones commences at the fourth transition time and ends at a fixed time relative to the fourth transition time. In a third example of the method, which optionally includes one or both of the first and second examples, determining when each of the plurality of transition times are estimated to occur based on the contrast signal comprises entering the contrast signal as input to a machine learning model, the machine learning model configured to output one or more of an arterial inflow function (AIF) curve, a venous outflow function (VOF) curve, and a tissue uptake curve (TUC), and determining when each of the plurality of transition times are estimated to occur based on one or more of the AIF curve, the VOF curve, and the TUC. In a fourth example of the method, which optionally includes one or more or each of the first through third examples, determining when each of the plurality of transition times are estimated to occur based on the contrast signal comprises entering the contrast signal as input to a machine learning model, the machine learning model configured to output a plurality of estimated time points, including one or more of an estimated arterial ascent knee time, an estimated arterial peak time, an estimated venous peak time, an estimated venous return to baseline time, an estimated tissue uptake ascent knee, an estimated tissue uptake peak, an estimated tissue uptake descent knee, and determining when each of the plurality of transition times are estimated to occur based on the plurality of estimated time points. In a fifth example of the method, which optionally includes one or more or each of the first through fourth examples, determining when each of the plurality of transition times are estimated to occur based on the plurality of estimated time points comprises: determining when the first transition time is estimated to occur as a function of the estimated arterial ascent knee time; determining when the second transition time is estimated to occur as a function of the estimated arterial peak time; determining when the third transition time is estimated to occur as a function of the estimated venous peak time; and determining when the fourth transition time is estimated to occur as a function of the estimated venous return to baseline time. In a sixth example of the method, which optionally includes one or more or each of the first through fifth examples, commanding initiation of the second injection at the time determined based on the contrast signal comprises commanding initiation of the second injection at an estimated venous return to baseline of the first injection, the estimated venous return to baseline of the first injection corresponding to the estimated venous return to baseline time output by the machine learning model.

An embodiment for a system is provided, including an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: upon an injection of a contrast agent, process projection data of a monitoring area of the subject from the DAS to measure a contrast signal of the contrast agent; determine when each of five zones of a contrast scan are estimated to occur based on the contrast signal; generate a scan prescription for the contrast scan based on when each of the five zones are estimated to occur, the scan prescription including one or more settings for the x-ray source, detector, and/or DAS that change between at least two zones of the five zones; and perform the contrast scan according to the scan prescription. In a first example of the system, the non-transitory memory stores a machine learning model configured to determine when each of the five zones are estimated to occur based on the contrast signal. In a second example of the system, which optionally includes the first example, the machine learning model is a regression model. In a third example of the system, which optionally includes one or both of the first and second examples, the machine learning model is a neural network.

An embodiment for a method is provided, the method including, upon an injection of a contrast agent, performing a plurality of perfusion acquisitions of a first anatomical region of interest (ROI) of a subject with the imaging system; processing projection data of the first anatomical ROI obtained from the plurality of perfusion acquisitions to measure a contrast signal of the contrast agent; performing a plurality of angiography acquisitions, each angiography acquisition performed at a respective time determined based on the contrast signal; and performing one or more additional perfusion acquisitions between each angiography acquisition. In a first example of the method, the plurality of angiography acquisitions includes a first angiography acquisition of a second anatomical ROI, a second angiography acquisition of the first anatomical ROI, and a third angiography acquisition of the first anatomical ROI. In a second example of the method, which optionally includes the first example, the one or more additional perfusion acquisitions are of first anatomical ROI. In a third example of the method, which optionally includes one or both of the first and second examples, performing the plurality of angiography acquisitions comprises performing the first angiography acquisition at an estimated arterial peak of the contrast agent, performing the second angiography acquisition at an estimated venous peak of the contrast agent, and performing the third angiography acquisition at an estimated venous return to baseline of the contrast agent. In a fourth example of the method, which optionally includes one or more or each of the first through third examples, the method further includes entering the contrast signal as input to a machine learning model trained to output the estimated arterial peak, the estimated venous peak, and the estimated venous return to baseline. In a fifth example of the method, which optionally includes one or more or each of the first through fourth examples, the plurality of angiography acquisitions are performed at a higher x-ray tube current than the plurality of perfusion acquisitions and/or at a higher x-ray tube voltage than the plurality of perfusion acquisitions. In a sixth example of the method, which optionally includes one or more or each of the first through fifth examples, processing projection data of the first anatomical ROI obtained from the plurality of perfusion acquisitions to measure the contrast signal comprises reconstructing a plurality of images from the projection data, segmenting a tissue of interest in each image of the plurality of images, measuring a signal intensity of the segmented tissue in each image relative to a baseline, and plotting each signal intensity as a function of time to generate the contrast signal. In a seventh example of the method, which optionally includes one or more or each of the first through sixth examples, the method further includes performing one or more final perfusion acquisitions after performing the plurality of angiography acquisitions, and wherein each of the plurality of angiography acquisitions, each of the plurality of perfusion acquisitions, each of the one or more additional perfusion acquisitions, and each of the one or more final perfusion acquisitions is performed without any additional injections of the contrast agent. In an eighth example of the method, which optionally includes one or more or each of the first through seventh examples, the method further includes reconstructing one or more diagnostic perfusion images from projection data acquired during the plurality of perfusion acquisitions and one or more additional perfusion acquisitions, and reconstructing one or more diagnostic angiography images from projection data acquired during the plurality of angiography acquisitions.

Another embodiment for a method is provided, the method including upon an injection of a contrast agent, performing an angiography scan while also performing a perfusion scan during a single scanning session, the angiography scan including a plurality of angiography acquisitions each performed at a respective time determined based on a contrast signal, the contrast signal measured from a plurality of images reconstructed from projection data acquired during at least a first portion of the perfusion scan. In a first example of the method, the method further includes inputting the contrast signal to a machine learning model, the machine learning model configured to output the respective times. In a second example of the method, which optionally includes the first example, the perfusion scan includes a plurality of perfusion acquisitions, the plurality of images reconstructed from projection data acquired during at least a first portion of the plurality of perfusion acquisitions, the first portion of the plurality of perfusion acquisitions performed at a first acquisition rate and a second portion of the plurality of perfusion acquisitions performed at a second acquisition rate, and wherein a transition time between the first portion of the plurality of perfusion acquisitions and the second portion of the plurality of perfusion acquisitions is determined based on the contrast signal. In a third example of the method, which optionally includes one or both of the first and second examples, the first portion of the plurality of perfusion acquisitions is performed with a table supporting the subject at a first position, and further comprising prior to performing a first angiography acquisition of the plurality of angiography acquisitions, moving the table from the first position to a second position, and after performing the first angiography acquisition, moving the table back to the first position and performing the second portion of the plurality of perfusion acquisitions with the table at the first position. In a fourth example of the method, which optionally includes one or more or each of the first through third examples, the first portion of the plurality of perfusion acquisitions is performed with an x-ray tube current at a first current, and the method further includes, prior to performing a first angiography acquisition of the plurality of angiography acquisitions, increasing the x-ray tube current to a second current and performing the first angiography acquisition at the second current, and after performing the first angiography acquisition, decreasing the tube current back to the first current and performing the second portion of the plurality of perfusion acquisitions at the first current.

An embodiment for a system is provided, including an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: upon an injection of a contrast agent, activate the x-ray source to perform a plurality of perfusion acquisitions of a first anatomical region of interest (ROI) of the subject; process projection data of the anatomical ROI of the subject received by the detector and sampled by the DAS to measure a contrast signal of the contrast agent; activate the x-ray source to perform a plurality of angiography acquisitions, each angiography acquisition performed at a respective time determined based on the contrast signal; and activate the x-ray source to perform one or more additional perfusion acquisitions between each angiography acquisition. In a first example of the system, the instructions, when executed, further cause the computer to reconstruct one or more diagnostic perfusion images from projection data acquired with the detector and sampled by the DAS during the perfusion acquisitions. In a second example of the system, which optionally includes the first example, the instructions, when executed, further cause the computer to reconstruct one or more diagnostic angiography images from projection data acquired with the detector and sampled by the DAS during the angiography acquisitions. In a third example of the system, which optionally includes one or both of the first and second examples, the non-transitory memory stores a machine learning model configured to determine the respective times at which each of the plurality of angiography acquisitions is to be performed based on the contrast signal. In a fourth example of the system, which optionally includes one or more or each of the first through third examples, the machine learning model is a regression model. In a fifth example of the system, which optionally includes one or more or each of the first through fourth examples, the machine learning model is a neural network.

An embodiment for a method is provided, the method including, upon an injection of a contrast agent, processing acquired projection data of an anatomical region of interest (ROI) of a subject to measure a contrast signal of the contrast agent; determining when each of a plurality of zones of a contrast scan are estimated to occur based on the contrast signal; updating a scan prescription for the contrast scan based on when each of the plurality of zones of the scan protocol are estimated to occur; and performing the contrast scan according to the updated scan prescription. In a first example of the method, determining when each of the plurality of zones are estimated to occur based on the contrast signal comprises determining a plurality of estimated transition times between zones, including an estimated first transition time when a first zone is estimated to transition to a second zone and an estimated second transition time when the second zone is estimated to transition to a third zone. In a second example of the method, which optionally includes the first example, the scan prescription includes a default setting for a scan parameter during the first zone and wherein updating the scan prescription includes adjusting when the default setting of the scan parameter is to be adjusted to a first setting based on the first transition time. In a third example of the method, which optionally includes one or both of the first and second examples, the scan parameter includes a frame rate. In a fourth example of the method, which optionally includes one or more or each of the first through third examples, updating the scan prescription further includes adjusting when the first setting is to be adjusted to a second setting based on the second transition time. In a fifth example of the method, which optionally includes one or more or each of the first through fourth examples, the acquired projection data of the anatomical ROI used to measure the contrast signal is acquired during the first zone. In a sixth example of the method, which optionally includes one or more or each of the first through fifth examples, processing projection data of the anatomical ROI to measure the contrast signal comprises reconstructing a plurality of images from the projection data, segmenting a tissue of interest in each image of the plurality of images, measuring a signal intensity of the segmented tissue in each image relative to a baseline, and plotting each signal intensity as a function of time to generate the contrast signal. In a seventh example of the method, which optionally includes one or more or each of the first through sixth examples, determining the plurality of estimated transition times between zones based on the contrast signal comprises entering the contrast signal as input to a machine learning model configured to output a plurality of time points of an arterial inflow function curve, a tissue uptake curve, and/or a venous outflow curve based on the contrast signal, and wherein each estimated transition time is determined as a function of a respective one of the plurality of time points.

Another embodiment for a method is provided, the method including, upon an injection of a contrast agent, initiating a contrast scan of an anatomical region of interest (ROI) of a subject; processing projection data of the anatomical ROI acquired during a first zone of the contrast scan to measure a contrast signal of the contrast agent; determining when a first transition time between the first zone and a second zone is estimated to occur and when each of one or more additional transition times between respective additional zones of the contrast scan are estimated to occur based on the contrast signal; and adjusting one or more scan parameters as the contrast scan progresses based on the first transition time and/or one or more additional transition times. In a first example of the method, adjusting one or more scan parameters as the contrast scan progresses comprises increasing a frame rate from a default frame rate to a first frame rate at the first transition time. In a second example of the method, which optionally includes the first example, the one or more additional transitions times includes a second transition time between the second zone and a third zone, and wherein adjusting one or more scan parameters as the contrast scan progresses comprises decreasing the frame rate from the first frame rate to a second frame rate at the second transition time. In a third example of the method, which optionally includes one or both of the first and second examples, determining when the first transition time and the one or more additional transition times are estimated to occur based on the contrast signal comprises entering the contrast signal as input to a machine learning model, the machine learning model configured to output a plurality of estimated time points, including an estimated arterial peak time, an estimated venous peak time, and an estimated venous return to baseline time, and determining when the first transition time and the one or more additional transition times are estimated to occur based on the plurality of estimated time points. In a fourth example of the method, which optionally includes one or more or each of the first through third examples, determining when the first transition time and the one or more additional transition times are estimated to occur based on the plurality of estimated time points comprises: determining when the first transition time is estimated to occur as a function of the estimated arterial peak time; determining when a second transition time is estimated to occur as a function of the estimated venous peak time; and determining when a third transition time is estimated to occur as a function of the estimated venous return to baseline time. In a fifth example of the method, which optionally includes one or more or each of the first through fourth examples, the contrast scan is a perfusion scan, and further comprising performing acquisitions of an angiography scan in between acquisitions of the perfusion scan. In a sixth example of the method, which optionally includes one or more or each of the first through fifth examples, performing acquisitions of the angiography scan in between acquisitions of the perfusion scan comprises performing the acquisitions of the angiography scan at select times determined based on the contrast signal.

An embodiment for a system is provided, including an x-ray source that emits a beam of x-rays toward a subject to be imaged; a detector that receives the x-rays attenuated by the subject; a data acquisition system (DAS) operably connected to the detector; and a computer operably connected to the DAS and configured with instructions in non-transitory memory that when executed cause the computer to: upon an injection of a contrast agent, initiate a contrast scan of an anatomical region of interest (ROI) of the subject; process projection data from the DAS during a first zone of the contrast scan to measure a contrast signal of the contrast agent; determine when each of a plurality of additional zones of the contrast scan are estimated to occur based on the contrast signal; and adjust one or more scan parameters as the contrast scan progresses based on when each of the plurality of additional zones of the contrast scan are estimated to occur. In a first example of the system, the contrast scan includes four zones, and wherein adjusting one or more scan parameters as the contrast scan progresses based on when each of the plurality of additional zones of the contrast scan are estimated to occur includes: adjusting a frame rate from a default frame rate to a first frame rate when transitioning from the first zone to a second zone; adjusting the frame rate from the first frame rate to a second frame rate when transitioning from the second zone to a third zone; and adjusting the frame rate from the second frame rate to a third frame rate when transitioning from the third zone to a fourth zone. In a second example of the system, which optionally includes the first example, the non-transitory memory stores a machine learning model configured to determine when each of a plurality of additional zones are estimated to occur based on the contrast signal. In a third example of the system, which optionally includes one or both of the first and second examples, the machine learning model is a regression model. In a fourth example of the system, which optionally includes one or more or each of the first through third examples, the machine learning model is a neural network.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method, comprising:
upon a first injection of a contrast agent, processing acquired projection data of a monitoring area of a subject to measure a contrast signal of the contrast agent;
entering the contrast signal as input to a machine learning model, the machine learning model configured to output one or more estimated contrast enhancement curves of the subject or one or more estimated contrast enhancement time points of the subject;
determining when each of a plurality of zones of a contrast scan are estimated to occur based on the output of the machine learning model;
generating a scan prescription for the contrast scan based on when each of the plurality of zones are estimated to occur; and
upon a second injection of contrast agent, performing the contrast scan according to the scan prescription.

2. The method of claim 1, wherein determining when each of the plurality of zones of the scan protocol are estimated to occur based on the contrast signal comprises determining a plurality of estimated transition times between zones, including an estimated first transition time when a first zone is estimated to transition to a second zone, an estimated second transition time when the second zone is estimated to transition to a third zone, an estimated third transition time when the third zone is estimated to transition to a fourth zone, and an estimated fourth transition time when the fourth zone is estimated to transition to a fifth zone.

3. The method of claim 2, wherein the plurality of estimated transition times are estimated from an arterial inflow function (AIF) curve and a venous outflow function (VOF) curve output from the machine learning model.

4. The method of claim 1, wherein the scan prescription includes at least one acquisition per zone acquired with one or more scan parameters, wherein generating the scan prescription includes setting the one or more scan parameters for each zone, and wherein at least one of the one or more scan parameters change between at least two zones of the plurality of zones.

5. The method of claim 4, wherein setting the one or more scan parameters for each zone comprises setting a frame rate and a tube current for each zone, wherein at least two zones of the plurality of zones differ in one or more of the frame rate and the tube current.

6. The method of claim 1, wherein performing the contrast scan comprises commanding initiation of the second injection of the contrast agent and then performing the at least one contrast scan acquisition per zone according to the scan prescription.

7. The method of claim 6, wherein commanding initiation of the second injection includes commanding initiation of the second injection at a target time relative to the first injection, the target time determined based on the contrast signal.

8. The method of claim 1, wherein the monitoring area is an artery and the contrast signal comprises a segment of an arterial inflow function (AIF) curve, wherein the segment starts at a first time corresponding to commencement of the first contrast injection and ends at a second time corresponding to a point of the AIF curve prior to a peak of the AIF curve, and wherein determining when each of the plurality of zones of the contrast scan are estimated to occur based on the contrast signal comprises determining when each of the plurality of zones of the contrast scan are estimated to occur based on the segment of the AIF curve.

9. The method of claim 1, wherein the monitoring area comprises brain parenchyma of the subject and the contrast signal comprises a segment of a tissue uptake curve, wherein the segment starts at a first time corresponding to commencement of the first contrast injection and ends at a second time corresponding to a point of the tissue uptake curve prior to a peak of the tissue uptake, and wherein determining when each of the plurality of zones of the contrast scan are estimated to occur based on the contrast signal comprises determining when each of the plurality of zones of the contrast scan are estimated to occur based on the segment of the tissue uptake curve.

10. A method for an imaging system, comprising:
upon a first injection of a contrast agent, processing acquired projection data of a monitoring area of a subject to measure a contrast signal of the contrast agent;
entering the contrast signal as input to a machine learning model, the machine learning model configured to output one or more estimated contrast enhancement curves of the subject or one or more estimated contrast enhancement time points of the subject;
determining when each of a plurality of transition times between respective zones of a plurality of zones of a contrast scan are estimated to occur based on the output of the machine learning model;
generating a scan prescription for the contrast scan based on when each of the plurality of transition times are estimated to occur, including for at least a first transition time of the plurality of transition times, adjusting a frame rate of the imaging system from a first frame rate to a second frame rate at the first transition time;
commanding initiation of a second injection of the contrast agent at a time determined based on the output of the machine learning model; and
upon initiation of the second injection, performing the contrast scan with the imaging system according to the scan prescription.

11. The method of claim 10, wherein the plurality of zones includes five zones and the plurality of transition times includes the first transition time and three additional transition times.

12. The method of claim 11, wherein a first zone of the five zones commences upon initiation of the second injection and ends at the first transition time, a second zone of the five zones commences at the first transition time and ends at a second transition time, a third zone of the five zones commences at the second transition time and ends at a third transition time, a fourth zone of the five zones commences at the third transition time and ends at a fourth transition time, and a fifth zone of the five zones commences at the fourth transition time and ends at a fixed time relative to the fourth transition time.

13. The method of claim 12, wherein the machine learning model is configured to output one or more of an arterial inflow function (AIF) curve, a venous outflow function (VOF) curve, and a tissue uptake curve (TUC) of the subject, and wherein determining when each of the plurality of transition times are estimated to occur comprises determining when each of the plurality of transition times are estimated to occur based on one or more of the AIF curve, the VOF curve, and the TUC.

14. The method of claim 12, wherein the machine learning model is configured to output the one or more estimated contrast enhancement time points of the subject, including one or more of an estimated arterial ascent knee time, an estimated arterial peak time, an estimated venous peak time, an estimated venous return to baseline time, an estimated tissue uptake ascent knee, an estimated tissue uptake peak, an estimated tissue uptake descent knee of the subject, and wherein determining when each of the plurality of transition times are estimated to occur comprises determining when each of the plurality of transition times are estimated to occur based on the one or more of the estimated contrast enhancement time points.

15. The method of claim 14, wherein determining when each of the plurality of transition times are estimated to occur comprises:
determining when the first transition time is estimated to occur as a function of the estimated arterial ascent knee time;
determining when the second transition time is estimated to occur as a function of the estimated arterial peak time;
determining when the third transition time is estimated to occur as a function of the estimated venous peak time; and
determining when the fourth transition time is estimated to occur as a function of the estimated venous return to baseline time.

16. The method of claim 14, wherein commanding initiation of the second injection at the time determined based on the output of the machine learning model comprises commanding initiation of the second injection at an estimated venous return to baseline of the first injection, the estimated venous return to baseline of the first injection corresponding to the estimated venous return to baseline time output by the machine learning model.

17. A system, comprising:
an x-ray source that emits a beam of x-rays toward a subject to be imaged;
a detector that receives the x-rays attenuated by the subject;
a data acquisition system (DAS) operably connected to the detector; and
a computer operably connected to the DAS and configured with instructions in non-transitory memory that when executed cause the computer to:
upon an injection of a contrast agent, process projection data of a monitoring area of the subject from the DAS to measure a contrast signal comprising a segment of a contrast enhancement curve of the contrast agent of the subject, wherein the segment terminates at or before a descent knee of the contrast enhancement curve;

enter the contrast signal as input to a machine learning model that is configured to output one or more estimated contrast enhancement curves of the subject or one or more estimated contrast enhancement time points of the subject;

determine when each of five zones of a contrast scan are estimated to occur based on the output of the machine learning model;

generate a scan prescription for the contrast scan based on when each of the five zones are estimated to occur, the scan prescription including one or more settings for the x-ray source, detector, and/or DAS that change between at least two zones of the five zones; and perform the contrast scan according to the scan prescription.

18. The system of claim 17, wherein the non-transitory memory stores the machine learning model.

19. The system of claim 18, wherein the machine learning model is a regression model.

20. The system of claim 18, wherein the machine learning model is a neural network, and wherein the segment terminates at or before a peak of the contrast enhancement curve.

* * * * *